United States Patent
Fukushima et al.

(10) Patent No.: US 10,357,330 B2
(45) Date of Patent: Jul. 23, 2019

(54) MEDICAL SUPPORT ARM DEVICE AND MEDICAL SYSTEM

(71) Applicant: SONY CORPORATION, Tokyo (JP)

(72) Inventors: Tetsuharu Fukushima, Tokyo (JP); Wataru Kokubo, Tokyo (JP); Toshimitsu Tsuboi, Tokyo (JP); Yohei Kuroda, Tokyo (JP); Yasuhisa Kamikawa, Tokyo (JP)

(73) Assignee: Sony Corporation, Tokyo (JP)

( * ) Notice: Subject to any disclaimer, the term of this patent is extended or adjusted under 35 U.S.C. 154(b) by 70 days.

(21) Appl. No.: 15/541,077

(22) PCT Filed: Feb. 1, 2016

(86) PCT No.: PCT/JP2016/000509
§ 371 (c)(1),
(2) Date: Jun. 30, 2017

(87) PCT Pub. No.: WO2016/132689
PCT Pub. Date: Aug. 25, 2010

(65) Prior Publication Data
US 2018/0014906 A1    Jan. 18, 2018

(30) Foreign Application Priority Data

Feb. 18, 2015 (JP) ................................ 2015-029473
Oct. 23, 2015 (JP) ................................ 2015-208534

(51) Int. Cl.
*A61B 90/50*    (2016.01)
*G02B 23/24*    (2006.01)
(Continued)

(52) U.S. Cl.
CPC ........... *A61B 90/50* (2016.02); *B25J 19/0004* (2013.01); *G02B 21/0012* (2013.01);
(Continued)

(58) Field of Classification Search
CPC .. A61B 90/50; B25J 19/0004; G02B 21/0012; G02B 21/36; G02B 23/2484; H04N 5/63
See application file for complete search history.

(56) References Cited

U.S. PATENT DOCUMENTS 4,548,373 A * 10/1985 Komura ................. A61B 6/105
                                                   188/171
6,246,200 B1     6/2001 Blumenkranz et al.
(Continued)

FOREIGN PATENT DOCUMENTS

EP    1 520 548 A2    4/2005
JP    2004-306159 A    11/2004

OTHER PUBLICATIONS

International Search Report dated Apr. 29, 2016, in PCT/JP2016/000509 filed Feb. 1, 2016.

*Primary Examiner* — Nelson D. Hernández Hernández
(74) *Attorney, Agent, or Firm* — Oblon, McClelland, Maier & Neustadt, L.L.P.

(57) ABSTRACT

There is provided a medical support arm device including a brake provided in at least one joint of a plurality of joints that define a deployment configuration of a multi-joint arm, and configured to release a rotation shaft of the at least one joint when electricity is supplied to the multi-joint arm and lock the rotation shaft when electricity is not supplied to the multi-joint arm. When electricity is not supplied the brake is configured to exert a brake force that supports a weight of the multi-joint arm to maintain the deployment configuration of the multi-joint arm, but also permits rotation of the rotation shaft by an external manually applied force equal to or larger than a predetermined value.

20 Claims, 8 Drawing Sheets

(51) Int. Cl.
   *G02B 21/00* (2006.01)
   *H04N 5/63* (2006.01)
   *G02B 21/36* (2006.01)
   *B25J 19/00* (2006.01)
   *A61B 90/00* (2016.01)
   *A61B 1/00* (2006.01)

(52) U.S. Cl.
   CPC ......... *G02B 21/36* (2013.01); *G02B 23/2484* (2013.01); *H04N 5/63* (2013.01); *A61B 1/0016* (2013.01); *A61B 1/00149* (2013.01); *A61B 90/361* (2016.02); *A61B 2090/508* (2016.02); *H04N 2201/02485* (2013.01)

(56) References Cited

U.S. PATENT DOCUMENTS

| | | | |
|---|---|---|---|
| 6,441,577 B2 * | 8/2002 | Blumenkranz | B25J 9/1689 128/DIG. 7 |
| 7,556,626 B2 * | 7/2009 | Ueda | A61B 90/50 600/102 |
| 2001/0013764 A1 | 8/2001 | Blumenkranz et al. | |
| 2002/0170791 A1 | 11/2002 | Saito et al. | |
| 2003/0117727 A1 * | 6/2003 | Weber | F16C 11/103 359/831 |
| 2003/0161159 A1 * | 8/2003 | Kupfer | A61B 90/35 362/402 |
| 2005/0075536 A1 | 4/2005 | Otsuka et al. | |

\* cited by examiner

[Fig. 1]
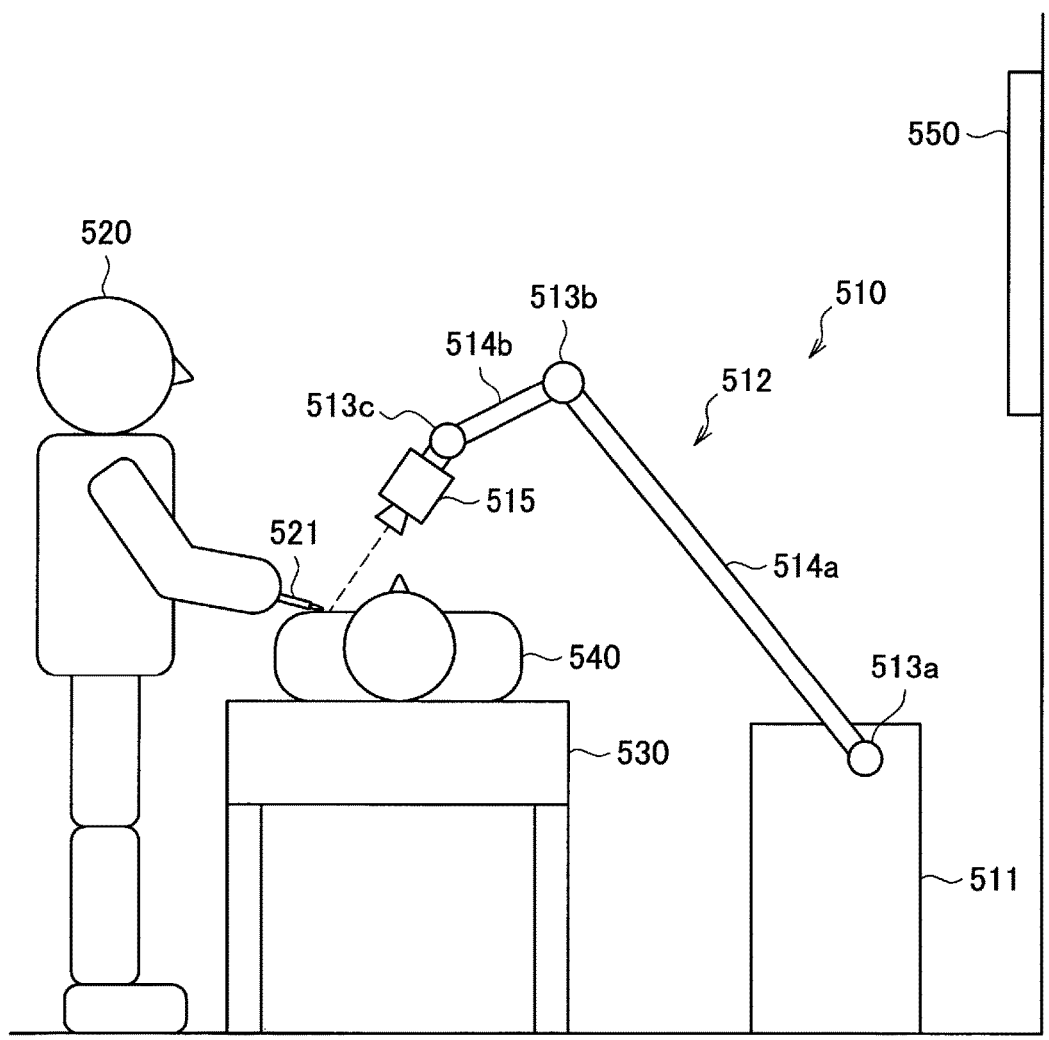

[Fig. 2]
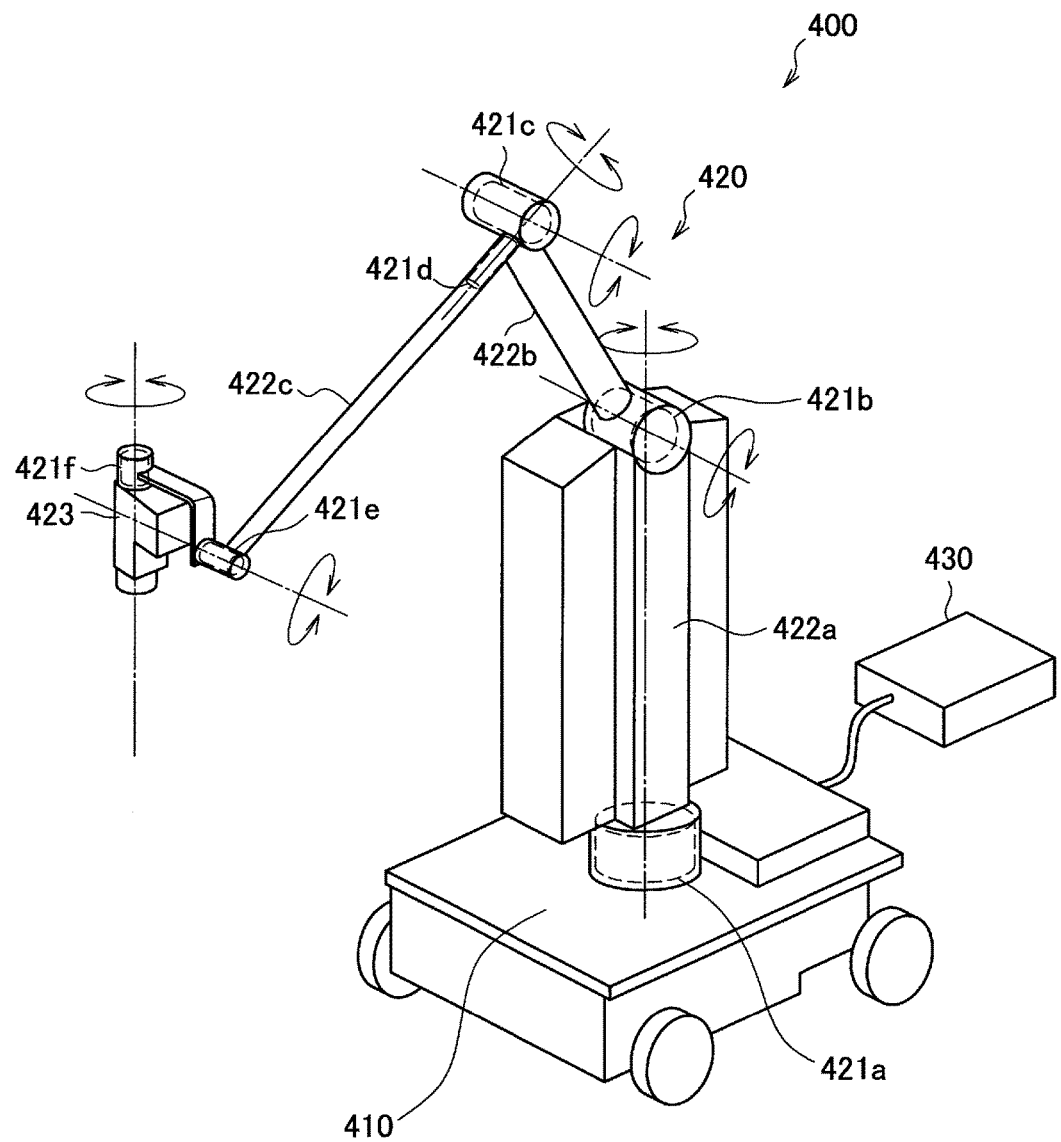

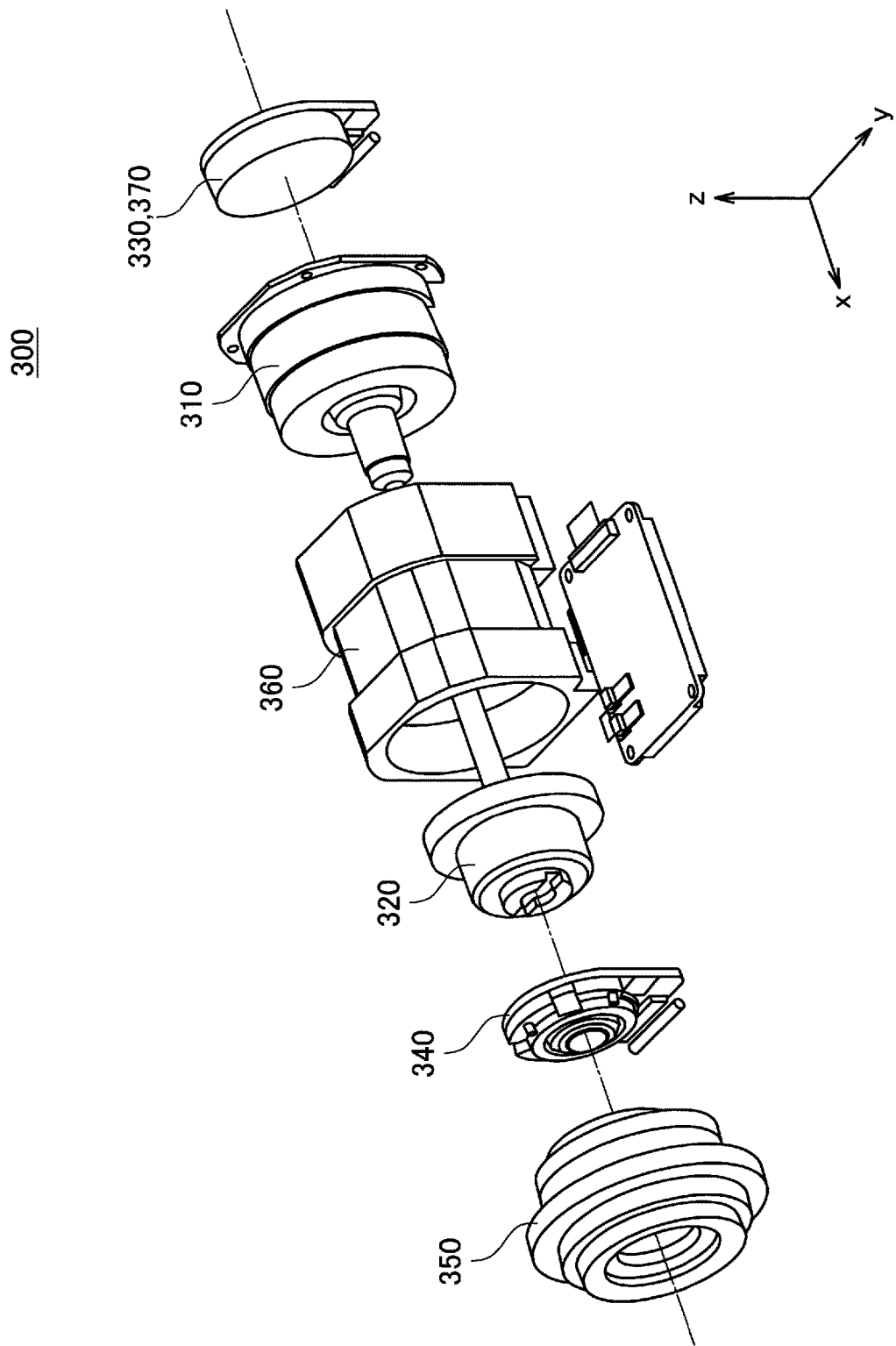
[Fig. 3]

[Fig. 4]
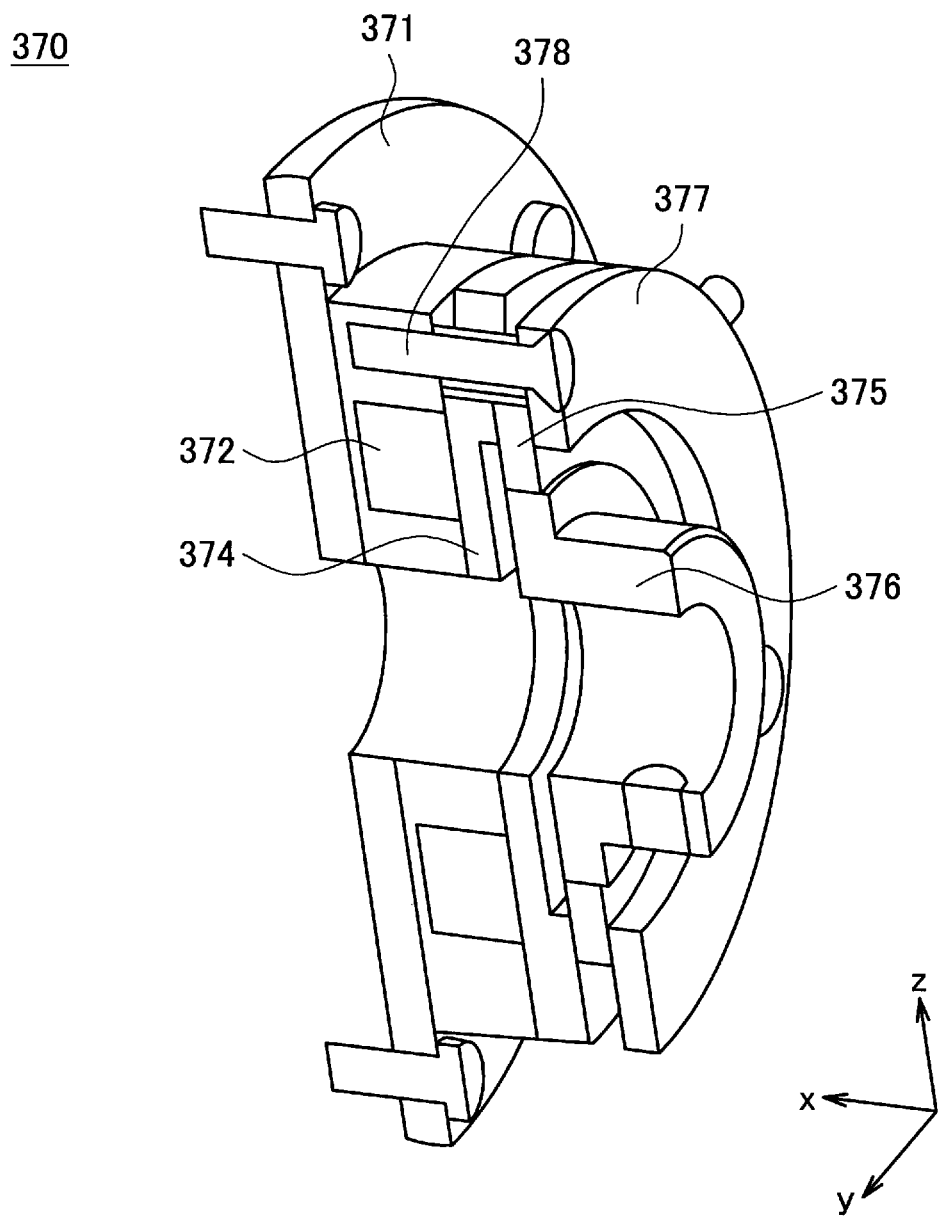

[Fig. 5]
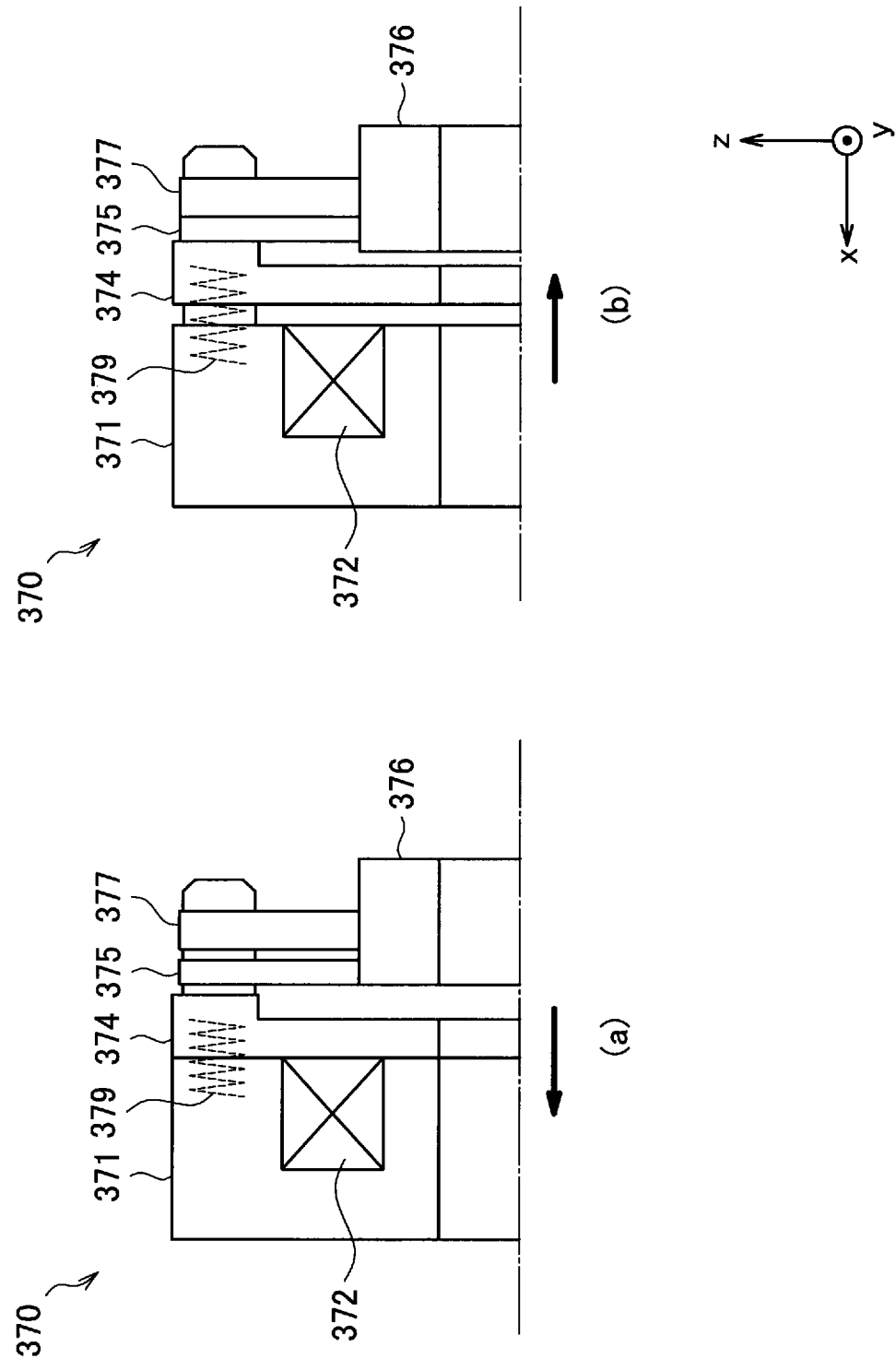

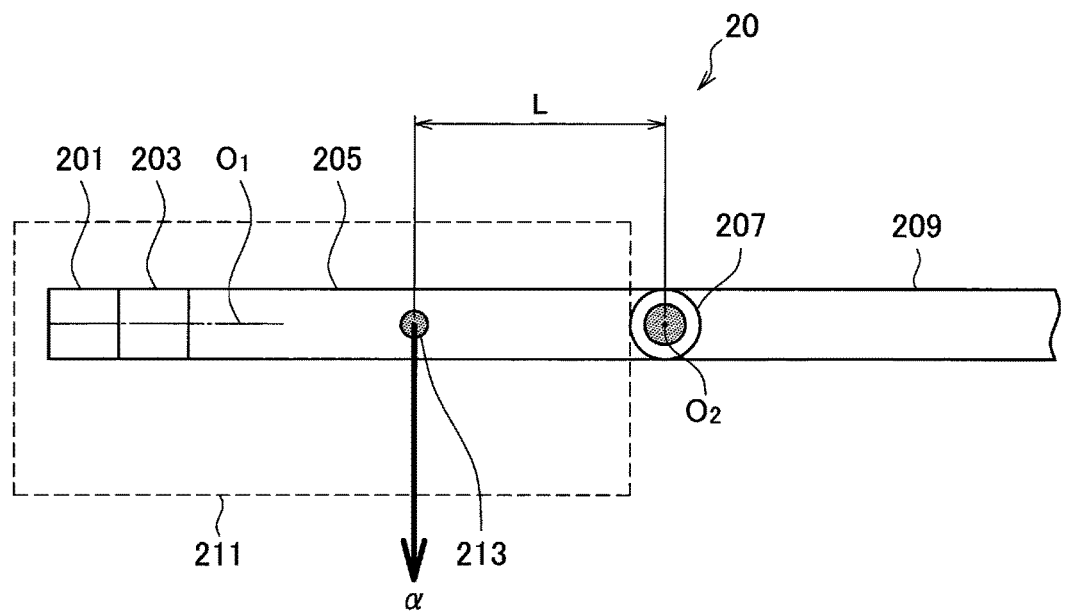
[Fig. 6]

[Fig. 7]
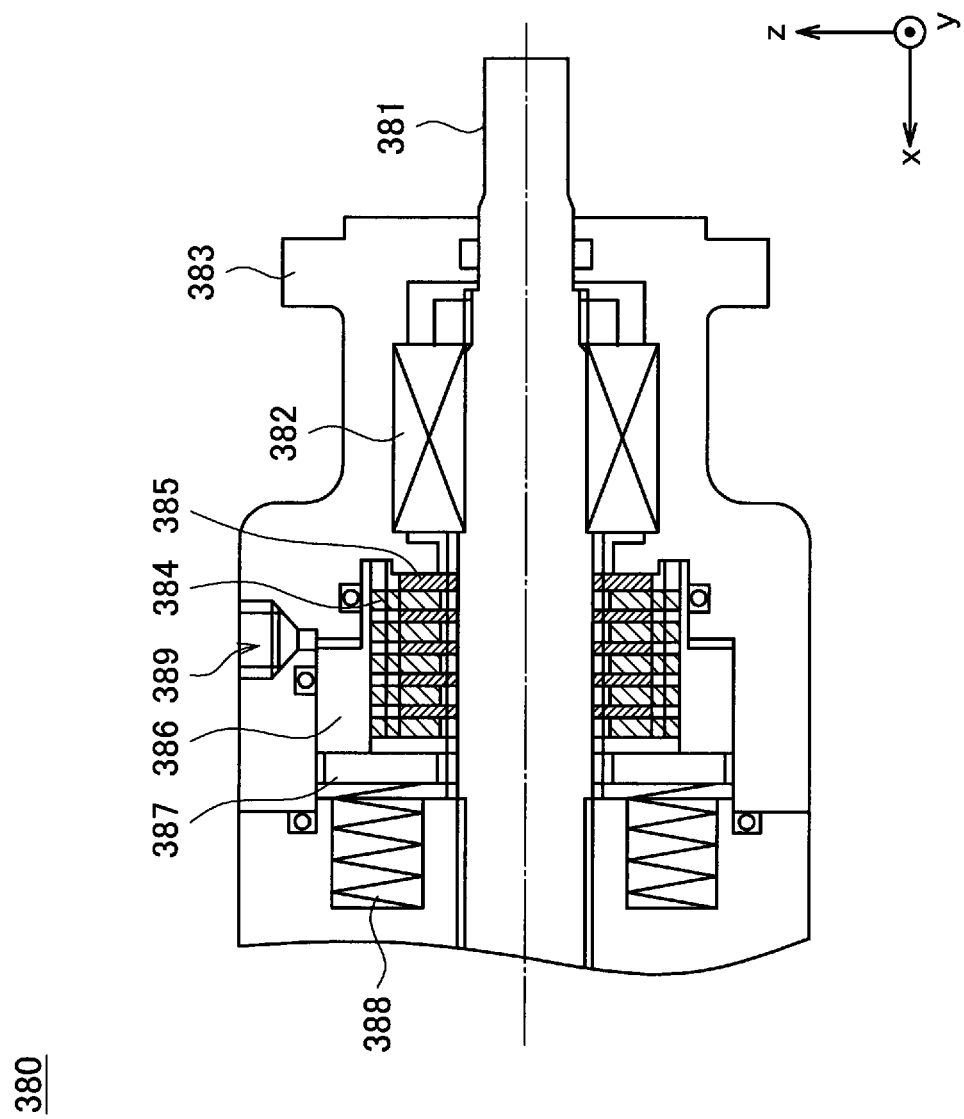

[Fig. 8]
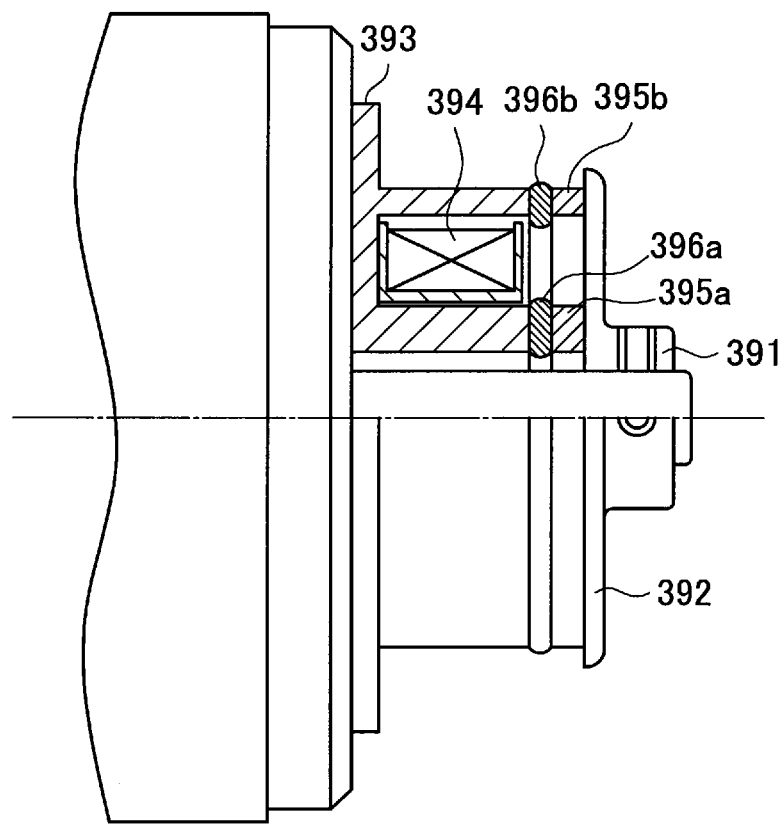

MEDICAL SUPPORT ARM DEVICE AND MEDICAL SYSTEM

CROSS REFERENCE TO RELATED APPLICATIONS

This application claims the benefit of Japanese Priority Patent Application JP 2015-029473 filed Feb. 18, 2015, and Japanese Priority Patent Application JP 2015-208534 filed Oct. 23, 2015, the entire contents of each of which are incorporated herein by reference.

TECHNICAL FIELD

The present disclosure relates to a medical support arm device and a medical system.

BACKGROUND ART

In recent years, support arm devices are used to support surgical operations at the medical front. For example, there is a proposed method in which an observation unit for observing a surgical site, such as a camera, is provided at a distal end of an arm unit of a support arm device, and a surgeon performs a surgical operation while watching an image captured by the observation unit. Alternatively, there is also a proposed method in which an operation tool, such as a forceps, is provided at the distal end of the arm unit, in order to cause the support arm device to perform a work that has been performed with human labor in the past, using the operation tool.

Here, in a support arm device including an actuator that is provided at each joint portion to be driven, the position and the orientation of the arm unit are controlled by controlling the driving state of a motor of the actuator. Thus, for example, when the supply of electric power to the actuator is cut off due to power outage or a similar reason, the motor is unable to be driven, which might result in a serious trouble, such as fall of the arm unit by its own weight. Thus, the support arm device having this drive mechanism is to stop safely when the electric power is cut off. Note that, in the following description, "support arm device" simply means a support arm device that can drive an arm unit by an actuator which is provided at at least one of joint portions of the arm unit, when there is no description particularly.

For example, in some industrial support arm devices used in a plant or the like, an actuator is provided with what is called a non-excitation operation electromagnetic brake that unlocks an output shaft of a motor when excited and locks the output shaft of the motor when demagnetized, in order to stop the arm unit in case of emergency, such as power outage (for example, Patent Literature 1). It might be possible to configure a safer medical support arm device by applying the technology used in this industrial support arm device to a medical support arm device.

CITATION LIST

Patent Literature

PTL 1: JP 2004-306159A

SUMMARY

Technical Problem

Here, in the industrial support arm device illustrated in above Patent Literature 1, an operator typically performs a work for unlocking brakes by supplying electric power repeatedly to the brakes of respective joint portions, when the brakes operate to fix the arm unit upon losing the power supply. Thus, when the electric power is unable to be supplied due to power outage or a similar reason for example, the arm unit is unable to be moved until the power supply is recovered, and the work using the support arm device is also stopped.

However, from the view point of safety, a medical support arm device is to perform basic movements even when the electric power is not supplied, in order to continue a surgical operation. If the surgical operation is stopped at an unexpected timing, there is a risk that a patient might be subject to danger.

In consideration of the above circumstances, with regard to the medical support arm device, there is a request for a technology that improves the safety more by achieving both of stopping safely when the supply of the electric power is cut off and continuing the surgical operation even when the power supply is lost. Thus, in the present disclosure, there is proposed a new and improved medical support arm device and a medical observation device capable of improving safety more.

Solution to Problem

According to an embodiment of the present disclosure, there is provided a medical support arm device including: a brake provided in at least one joint of a plurality of joints that define a deployment configuration of a multi-joint arm, and configured to release a rotation shaft of the at least one joint when electricity is supplied to the multi-joint arm and lock the rotation shaft when electricity is not supplied to the multi-joint arm. The brake, when electricity is not supplied to the multi-joint arm, is configured to exert a brake force that supports a weight of the multi-joint arm to maintain the deployment configuration of the multi-joint arm, but also permits rotation of the rotation shaft by an external manually applied force equal to or larger than a predetermined value.

According to an embodiment of the present disclosure, there is provided a medical system device including: a multi-joint arm including a plurality of joints; and a medical device provided at a distal end of the multi-joint arm to oppose a surgical site of a patient. At least one of the plurality of joints is provided with a brake configured to release a rotation shaft of the at least one joint when electricity is supplied and to lock the rotation shaft when electricity is not supplied. The brake is configured to support a weight of the multi-joint arm to maintain a deployment configuration of the multi-joint arm when electricity is not supplied, and apply a brake force that allows rotation of the rotation shaft by an external force equal to or larger than a predetermined value.

According to an embodiment of the present disclosure, each joint portion of the arm unit is provided with a brake configured to exert a brake force that supports a weight of the multi-joint arm to maintain the deployment configuration of the multi-joint arm, but also permits rotation of the rotation shaft by an external manually applied force equal to or larger than a predetermined value. Thus, when supply of electric power is disrupted due to power outage or a similar reason for example, the arm unit is stopped safely, and a process using the arm unit, such as a surgical operation, is executed continuously by moving the arm unit by manual operation. Thereby, a safer medical support arm device and medical observation device are provided.

Advantageous Effects of Invention

As described above, according to the embodiments of the present disclosure, the safety is improved more. Note that the above effect is not necessarily restrictive, but one of the effects described in the present specification or another effect that can be known from the present specification may be achieved in addition to the above effect or instead of the above effect.

BRIEF DESCRIPTION OF DRAWINGS

FIG. 1 is a schematic view illustrating how a surgical operation is performed using a support arm device according to an embodiment of the present disclosure.

FIG. 2 is a diagram illustrating an overall configuration of a support arm device according to the present embodiment.

FIG. 3 is an exploded perspective view illustrating one exemplary configuration of an actuator provided in each joint portion of a support arm device according to the present embodiment.

FIG. 4 is a perspective cross-sectional view illustrating a configuration of a brake mechanism (or simply a brake) according to the present embodiment.

FIG. 5 is an explanatory diagram for describing movement of a brake mechanism according to the present embodiment.

FIG. 6 is a diagram for describing a setting method of a brake force of a brake mechanism.

FIG. 7 is a cross-sectional view illustrating a configuration of a brake mechanism according to one exemplary variant of the present embodiment.

FIG. 8 is a cross-sectional view illustrating a configuration of a brake mechanism according to another exemplary variant of the present embodiment.

DESCRIPTION OF EMBODIMENTS

Hereinafter, preferred embodiments of the present disclosure will be described in detail with reference to the appended drawings. It should be noted that, in this specification and the appended drawings, structural elements that have substantially the same function and structure are denoted with the same reference numerals, and repeated explanation thereof is omitted.

Note that, description will be made in the following order.
1. Study on Medical Support Arm Device
2. Configuration of Support Arm Device
2-1. Overall Configuration
2-2. Configuration of Actuator
2-3. Configuration of Brake Mechanism
3. Specific Example of Setting Method of Brake Force
4. Exemplary Variant of Brake Mechanism
4-1. Brake Using Oil Hydraulic Cylinder
4-2. Brake Using Magnetic Fluid
5. Supplement
(1. Study on Medical Support Arm Device)

Before describing a configuration of a support arm device according to a preferable embodiment of the present disclosure in the detail, an exemplary application of the support arm device according to the present embodiment to surgical operation will be described, and various functions of the medical support arm device will be described, in order to make the present disclosure clearer.

With reference to FIG. 1, how a surgical operation is performed using the support arm device according to an embodiment of the present disclosure will be described. FIG. 1 is a schematic view illustrating how a surgical operation is performed using the support arm device according to an embodiment of the present disclosure.

FIG. 1 illustrates a situation in which a surgeon 520 performs a surgical operation to a patient 540 on an operating table 530, using a surgical operation tool 521 for a surgical operation, such as scalpel, tweezers, and forceps, for example. The support arm device 510 according to the present embodiment is provided beside the operating table 530. The support arm device 510 includes a base portion 511 which is a base platform, and an arm unit 512 (or multi-joint arm or power-assisted multi-joint arm) that extends from the base portion 511. Also, although not depicted, the support arm device 510 is provided with a control device for controlling movement of the support arm device 510 (corresponding to a control device 430 illustrated in FIG. 2 described later).

The arm unit 512 includes a plurality of joint portions (or joints) 513a, 513b, 513c, a plurality of links 514a, 514b coupled by the joint portions 513a, 513b, and an image capturing unit 515 provided at a distal end of the arm unit 512. The joint portions 513a to 513c are provided with an actuator 300 illustrated in FIG. 3 described later, and the joint portions 513a to 513c are configured rotatable with respect to a predetermined rotation axis by driving of the actuator 300. The driving of the actuator 300 is controlled by the above control device, in order to control the rotation angle of each joint portion 513a to 513c, and to control the driving of the arm unit 512.

Although in FIG. 1 the configuration of the arm unit 512 is depicted simply for simplicity, the numbers and the locations of the joint portions 513a to 513c and the links 514a, 514b, the direction of a drive shaft (a rotation shaft) of the joint portions 513a to 513c, and the like may be set as appropriate actually in such a manner that the arm unit 512 has a desired degree of freedom. For example, the arm unit 512 can be configured to have a degree of freedom that is equal to or greater than six degrees of freedom preferably. Thereby, the image capturing unit 515 is moved freely in the range of movement of the arm unit 512.

The image capturing unit 515 is an example of an observation unit for observing a surgical site of the patient 540, and is a camera capable of capturing a moving image and/or a still image of an image capturing target, for example. The image capturing unit 423 can be what is called a video microscope that enlarges an image capturing target as appropriate and captures a digital image thereof. Other examples of the observation unit are an endoscope, an optical microscope, or the like, for example. A support arm device provided with an observation unit for observing a surgical site of these patient 540 at the distal end of the arm unit 512 is also referred to as an observation device in the present specification.

As illustrated in FIG. 1, when performing a surgical operation, the spatial positions and the orientations (or deployment configurations) of the arm unit 512 and the image capturing unit 515 are controlled by the support arm device 510, in such a manner that the image capturing unit 515 provided at the distal end of the arm unit 512 captures an image of the surgical site of the patient 540. A display device 550 is installed in an operation room at a position opposite to the surgeon 520, and an image of a surgical site captured by the image capturing unit 515 is displayed on the display device 550. The surgeon 520 performs various types of operation, while observing the image of the surgical site displayed on the display device 550.

Note that the distal end unit provided at the distal end of the arm unit 512 is not limited to the observation unit such as the image capturing unit 515, but may be various types of the medical devices. The medical device can include various types of operation tools, such as forceps and retractor for example, in addition to the above observation unit. In the past, handling of these medical devices is performed by human labor, and thus there are many medical staff members in a surgical operation, but a surgical operation can be performed by fewer members by performing handling of these medical devices by the support arm device 510.

In the above, with reference to FIG. 1, how a surgical operation is performed using the support arm device 510 according to the present embodiment has been described. Although in the example illustrated in FIG. 1 the support arm device 510 is used in the surgical operation, the support arm device 510 may be used for the purpose of testing, when a unit for testing such as an endoscope is provided as the distal end unit for example.

Here, the support arm device 510 for medical care used in surgical operation and test described above is to be highly safe. The distal end unit attached to the distal end of the arm unit 512 illustrated as the image capturing unit 515 is located to touch the vicinity of the surgical site of the patient 540 or the surgical site directly during a surgical operation. Thus, for example, when a failure occurs in the control of the arm unit 512, and the control of the position and the orientation of the distal end unit becomes unstable, there is a risk that a patient might be subject to danger.

In particular, when the supply of the electric power is cut off due to power outage or a similar reason for example, the actuator provided in each joint portion 513a to 513c becomes unable to be driven, and thus, without taking measures it is possible to cause a serious trouble, such as the arm unit 512 falling by its own weight and hurting the patient 540. Thus, the support arm device 510 is to stop safely when the supply of the electric power is cut off.

However, simultaneously, the support arm device 510 is to be operable to perform basic movements to continue the surgical operation, even when the electric power is not supplied. If the surgical operation is stopped at an unexpected timing, there is a risk that a patient might be subject to danger.

As described above, a technology for improving safety more have been sought for the medical care support arm device 510 by stopping safely when the electric power is cut off and continuing the surgical operation when losing the power supply. As a result of study in consideration of the above circumstances, the present inventors have reached the support arm device 510 according to the preferable embodiment of the present disclosure.

Although detail will be described later in below (2-2. Configuration of Actuator), in the support arm device 510 according to the present embodiment, the actuator 300 of each joint portion 513a to 513c is provided with a brake mechanism that releases the rotation shaft of the joint portions 513a to 513c when electricity is supplied and locks the rotation shaft when electricity is not supplied. Then, the brake mechanism supports the weight of the arm unit 512 when electricity is not supplied to keep the orientation, and has a brake force that allows the movement of the rotation shaft by the external force equal to or larger than a predetermined value. Thereby, the support arm device 510 according to the present embodiment can stop safely when the electric power is cut off, and continue the surgical operation when losing the power supply.

In the following, the configuration of the support arm device 510 according to the present embodiment will be described in more detail.

(2. Configuration of Support Arm Device)
(2-1. Overall Configuration)

With reference to FIG. 2, the overall configuration of the support arm device according to the present embodiment will be described. FIG. 2 is a diagram illustrating the overall configuration of the support arm device according to the present embodiment.

Referring to FIG. 2, a support arm device 400 includes a base portion 410, an arm unit 420, and a control device 430. The support arm device 400 is a medical support arm device that is preferably applied to a surgical operation, a test, or the like, in the same way as the support arm device 510 illustrated in the above FIG. 1.

The base portion 410 is a base platform of the support arm device 400, and the arm unit 420 is extended from the base portion 410. Casters are provided in the base portion 410, and the support arm device 400 contacts with the floor surface via the casters, and moves on the floor surface by the casters. Note that, the configuration of the support arm device 400 according to the present embodiment is not limited to such an example, but for example the support arm device 400 may be configured without the base portion 410, and the arm unit 420 is directly attached to a ceiling or a wall surface of an operation room. For example, when the arm unit 420 is attached to the ceiling, the support arm device 400 is configured in such a manner that the arm unit 420 hangs down from the ceiling.

The arm unit 420 includes a plurality of joint portions 421a to 421f, a plurality of links 422a to 422c coupled each other by the joint portions 421a to 421f, and an image capturing unit 423 provided at the distal end of the arm unit 420.

The links 422a to 422c are rod-like members, and the one end of the link 422a is coupled with the base portion 410 via the joint portion 421a, and the other end of the link 422a is coupled with one end of the link 422b via the joint portion 421b, and further the other end of the link 422b is coupled with the one end of the link 422c via the joint portions 421c, 421d. Further, the image capturing unit 423 is coupled with the distal end of the arm unit 420, that is, the other end of the link 422c, via the joint portion 421e, 421f. As described above, the ends of the links 422a to 422c are coupled with each other by the joint portions 421a to 421f in order to configure an arm shape extended from the base portion 410 which is a support point.

The image capturing unit 423 is an example of the observation unit for observing the surgical site, and is a camera capable of capturing a moving image and/or a still image of an image capturing target for example. The image capturing unit 423 corresponds to the image capturing unit 515 illustrated in the above FIG. 1. An image of a surgical site of a patient captured by the image capturing unit 423 is enlarged as appropriate and is displayed on a display device (not illustrated in the drawings) provided in an operation room for example, and a surgeon performs a surgical operation while observing the image of the surgical site of the patient displayed on the display device. The image capturing unit 423 can be what is called a video microscope. As described above, the support arm device 400 can be the observation device 400 with the observation unit attached to the distal end of the arm unit 420. As described above, an endoscope, an optical microscope, or the like can be provided as an observation unit, in other examples. Note that, among the observation devices 400, the support arm device 400 provided with the image capturing unit 423 at the distal end of the arm unit 420 is referred to as a video microscope device 400.

Note that the distal end unit provided at the distal end of the arm unit 420 is not limited to the observation unit, but various types of the medical devices may be attached to the distal end of the arm unit 420 as the distal end unit. For example, various types of the operation tools, such as forceps and retractor, may be connected as the distal end unit. Alternatively, for example, an endoscope dedicated or microscope dedicated light source or a surgical operation dedicated energy device for sealing blood vessels may be connected as the distal end unit.

The joint portions 421a to 421f are provided with the actuator 300 illustrated in FIG. 3 described later, and the joint portions 421a to 421f are configured rotatable with respect to a predetermined rotation axis by driving of the actuator 300. The driving of the actuator 300 is controlled by the control device 430. The driving of the actuator 300 of each joint portion 421a to 421f is controlled to control the driving of the arm unit 420, such as stretching and shortening (folding) of the arm unit 420, for example.

Here, in the present embodiment, the actuator 300 of each joint portion 421a to 421f is provided with a brake mechanism that releases the rotation shaft of the joint portions 421a to 421f when electricity is supplied and locks the rotation shaft when electricity is not supplied. Then, the brake force of the brake mechanism is adjusted in such a manner to support the weight of the arm unit 420 to keep the orientation and allow the movement of the rotation shaft by the external force equal to or larger than a predetermined value, when electricity is not supplied. Moreover, the brake force is controllable adjusted to correspond with a change in gravitationally induced torque applied on the arm depending on a deployment configuration of the arm. Thereby, the support arm device 400 according to the present embodiment can stop safely when the electric power is cut off, and continue the surgical operation when losing the power supply. Note that the configuration of the actuator 300 and the brake mechanism will be described in below (2-2. Configuration of Actuator) in detail.

Note that, in the example illustrated in the drawings, the support arm device 400 includes the six joint portions 421a to 421f, to achieve six degrees of freedom with regard to the driving of the arm unit 420. The image capturing unit 423 is moved freely in the range of movement of the arm unit 420, by configuring the arm unit 420 with six degrees of freedom. Thereby, the image capturing unit 423 captures an image of a surgical site from various angles and distances. Note that the configuration of the arm unit 420 is not limited to the illustrated example, but the numbers and the locations of the joint portions 421a to 421f and the links 422a to 422c, the directions of the drive shafts of the joint portions 421a to 421f, or the like may be set as appropriate, in such a manner that the arm unit 420 has a desired degree of freedom. Note that the arm unit 420 preferably has a degree of freedom equal to or greater than six degrees of freedom, in consideration of the degree of freedom of the position and the orientation of the image capturing unit 423.

The control device 430 is configured with a processor such as a central processing unit (CPU) and a digital signal processor (DSP), a microcomputer in which these processors are mounted, or the like, for example, and controls the movement of the support arm device 400 by executing signal processing in accordance with a predetermined program.

Force control is used preferably in consideration of handling easiness of the arm unit 420, as the control method of the support arm device 400. In the force control, the driving of the actuator 300 can be controlled by the control device 430, and the movement of the arm unit 420 can be controlled, in such a manner that the arm unit 420 moves in the direction of the force exerted on the arm unit 420, in response to handling to move the arm unit 420, which is performed by a user who touches the arm unit 420 directly, for example. As described above, the force control enables the user to touch the arm unit 420 directly and move the arm unit 420, and therefore the handling is performed more easily and more intuitively. Note that various types of publicly known methods may be used as a specific control method of the support arm device 400 by the force control, and thus the detailed description will be omitted.

Note that the control method of the support arm device 400 is not limited to such an example, but the movement of the support arm device 400 may be controlled by other various types of publicly known control methods, such as position control, for example. When the support arm device 400 is controlled by the position control, the support arm device 400 can be provided with an input device such as a controller for handling the arm unit 420.

Although in the example illustrated in the drawings the control device 430 is connected to the base portion 410 via the cable, a control substrate or the like having the same function as the control device 430 may be provided in the inner portion of the base portion 410.

In the above, with reference to FIG. 2, the schematic configuration of the support arm device 400 according to the present embodiment has been described.

Here, in the present embodiment, the control device 430, can be provided with a function (a power supply control unit) for controlling the supply of the driving electric power to the arm unit 420 and the image capturing unit 423. Then, when the support arm device 400 is configured in such a manner that the driving of the arm unit 420 (that is, the driving of the actuator 300 of each joint portion 421a to 4210 and the driving of the image capturing unit 423 share the power supply, and an abnormality or a failure occurs in the electric power system, the power supply control unit controls to stop the electric power supply to the actuator 300 first, and continues the electric power supply to the image capturing unit 423 as long as possible preferably. That is, it is preferable that the support arm device 400 is designed such that the electric power is supplied to the image capturing unit 423 preferentially, when an abnormality or a failure occurs in the electric power system. When the electric power supply to the image capturing unit 423 is stopped, the surgical site becomes unable to be observed by the image capturing unit 423, and thus the surgical operation is difficult to continue. In contrast, in the present embodiment, because the brake mechanism 370 is provided, the orientation of the arm unit 420 is kept, and the arm unit 420 can be moved manually (e.g., by a hand of a user), in order to continue the surgical operation, even when the electric power supply to the actuator 300 is stopped. Thus, from the view point of continuing the surgical operation as long as possible for the safety of a patient, it is preferable that the electric power system of the support arm device 400 is configured such that the function of the image capturing unit 423 is continued as long as possible as described above.

(2-2. Configuration of Actuator)

With reference to FIG. 3, the configuration of the actuator provided in each joint portion 421a to 421f of the support arm device 400 illustrated in FIG. 2 will be described. FIG. 3 is an exploded perspective view illustrating one exemplary configuration of the actuator provided in each joint portion 421a to 421f of the support arm device 400 according to the present embodiment.

Referring to FIG. 3, the actuator 300 includes a motor 310, a speed reducer 320, an input shaft encoder 330, an output shaft encoder 340, an output shaft 350, a housing 360, and a brake mechanism 370. In the actuator 300, the rotation speed of the rotation shaft of the motor 310 is reduced by the speed reducer 320 at a predetermined speed reduction ratio and transmitted to another member of subsequent stage via and the output shaft 350, and thereby the other member is driven.

Note that, in the following description, the rotation shaft direction of the actuator is also referred to as x axis direction. Also, two directions orthogonal to each other in the flat plane perpendicular to x axis direction are referred to as y axis direction and z axis direction, respectively.

The housing 360 has a substantially cylindrical shape, and each component is contained in the inner portion. The actuator 300 containing each component in the housing 360 is integrated with each joint portion 421a to 421f of the above support arm device 400.

When a predetermined command value (a current value) is given, the motor 310 is a drive mechanism that generates the drive force by rotating the rotation shaft at the rotation speed corresponding to the command value. The motor 310 is a brushless motor, for example. Note that the present embodiment is not limited to such an example, but various types of publicly known devices may be used as the motor 310.

The speed reducer 320 is coupled with the rotation shaft of the motor 310. The speed reducer 320 reduces the rotation speed of the rotation shaft of the coupled motor 310 (that is, the rotation speed of the input shaft), at a predetermined speed reduction ratio and transmits it to the output shaft 350. In the present embodiment, the configuration of the speed reducer 320 is not limited to a specific one, but various types of publicly known ones may be used as the speed reducer 320. Note that it is preferable to use ones that can set the speed reduction ratio highly accurately, such as harmonic drive (registered trademark) for example, as the speed reducer 320. Also, the speed reduction ratio of the speed reducer 320 can be set as appropriate, depending on intended use of the actuator 300. For example, as in the present embodiment, when the actuator 300 is applied to the joint portions 421a to 421f of the support arm device 400, the speed reducer 320 having the speed reduction ratio of approximately 1:100 can be used preferably.

The input shaft encoder 330 detects the rotation angle of the input shaft (that is, the rotation angle of the motor 310). The output shaft encoder 340 detects the rotation angle of the output shaft 350. The configurations of the input shaft encoder 330 and the output shaft encoder 340 are not limited, but the input shaft encoder 330 and the output shaft encoder 340 may be, for example, various types of publicly known rotary encoders, such as a magnetic encoder and an optical encoder.

The brake mechanism 370 has a function for releasing the rotation shaft of the actuator 300 when electricity is supplied and locking the rotation shaft of the actuator 300 to stop the rotation when electricity is not supplied. In the example illustrated in the drawings, the brake mechanism 370 is configured integrally with the input shaft encoder 330, and is configured such that the rotation of the actuator 300 is stopped by locking the rotation shaft of the motor 310 (that is, the input shaft).

Note that the location of the brake mechanism 370 is not limited to the illustrated example, but the brake mechanism 370 may be located as a member separated from the input shaft encoder 330. Also, the brake mechanism 370 is needless to be provided in the input shaft necessarily, but may be provided in the output shaft 350. Note that, in the actuator 300, the speed reducer 320 is provided between the input shaft and the output shaft 350, and thus the torque of the output shaft 350 is relative large. Thus, when the brake mechanism 370 is provided in the output shaft 350, the brake mechanism 370 is to have a larger brake force, and thus it is possible that the brake mechanism 370 becomes larger. Thus, the actuator 300, that is, the joint portions 421a to 421f can be made smaller, by providing the brake mechanism 370 in the input shaft as illustrated in the drawing.

When the supply of the electric power is cut off, the brake force of the brake mechanism 370 is adjusted to support the weight of the arm unit 420 and keep the orientation of the arm unit 420. Thereby, even in the time of emergency such as power outage, the arm unit 420 is stopped safely.

Note that, in the present embodiment, in addition, the brake force of the brake mechanism 370 is adjusted to allow the rotation of the rotation shaft in response to the external force when the external force equal to or larger than a predetermined value is loaded, even when the electric power is cut off and the rotation shaft of the actuator 300 is locked. Thereby, even when the power supply is lost, the arm unit 420 can be moved with human labor, in order to continue the surgical operation. Note that the specific configuration of the brake mechanism 370 will be described in below (2-3. Configuration of Brake Mechanism) in detail.

Although in the present embodiment the brake mechanism 370 can be provided in all joint portions 421a to 421f to keep the orientation of the arm unit 420 when electricity is not supplied, the above brake force adjustment is needless to be performed in all of them. For example, the above brake force adjustment may be performed only for the brake mechanism 370 of the actuators 300 provided in the joint portions that achieve the movement for continuing the surgical operation, among the joint portions 421a to 421f. This is because, after starting the surgical operation, it is less likely to move the arm unit 420 to change the position of the distal end unit largely, and when the arm unit 420 is fixed due to power outage or a similar reason during the surgical operation for example, it is sufficient if only the joint portions, among the joint portions 421a to 421f, for defining the orientation of the distal end unit are be handled in response to the external force.

In the exemplary configuration illustrated in FIG. 2, the above brake force adjustment is performed only for the brake mechanisms 370 of the actuators 300 provided in the joint portions 421d to 421f, which are provided closer to the distal end and are the joint portions that define the orientation of the image capturing unit 423. In this case, the brake mechanism 370 of the actuator 300 provided in each remaining joint portion 421a to 421c may have a stronger brake force that fixes more firmly the position and the orientation of the arm unit 420 when electricity is not supplied. Thereby, only brake forces of a part of the brake mechanisms 370, among the brake mechanisms 370 provided in the arm unit 420, are adjusted, and the brake forces of other brake mechanisms 370 are needless to be designed in detail, and thus the design of the arm unit 420 is easier.

Also, when components of distal side that each joint portion 421d to 421f supports are balanced (that is, when the gravity center of the components of distal side is positioned on the rotation shaft of each joint portion 421d to 421f), the brake mechanism 370 is needless to be provided necessarily in the joint portions 421d to 421f. This is because the orientation of the arm unit 420 is kept without generating the brake force in the joint portion, when the components provided closer to the distal end than a certain joint portion for configuring the arm unit 420, which are to be supported by the joint portion, are balanced with respect to the joint portion.

For example, when the arm unit 420 is configured such that the rotation shaft in the joint portion 421f that supports the image capturing unit 423 is in substantially parallel with the optical axis of the image capturing unit 423 as in the exemplary configuration illustrated in FIG. 2, the brake mechanism 370 is needless to be provided in the joint portion 421f necessarily. This is because, in general, the image capturing unit 423 has a cylindrical shape in many cases, and the gravity center is positioned on the optical axis in many cases, and therefore, when the rotation shaft of the joint portion 421f is in substantially parallel with the optical axis of the image capturing unit 423 as described above, it is highly possible that the gravity center of the image capturing unit 423 is positioned on the rotation shaft of the joint portion 421f, that is, it is highly possible that the image capturing unit 423 is balanced in relation to the joint portion 421f. Thus, even when the brake mechanism 370 is not provided in the joint portion 421f, it is unlikely that the image capturing unit 423 moves (rotates) by its own weight when losing the power supply.

In the above, with reference to FIG. 3, the overall configuration of the actuator 300 according to the present embodiment has been described. Note that the actuator 300 may also include other components other than the depicted components. For example, the actuator 300 may also include various types of components that can be included in a general actuator, such as a driver circuit (a driver integrated circuit (IC)) that rotationally drives the motor 310 by supplying electrical current to the motor 310, and a torque sensor that detects the torque exerted on the output shaft 350. In particular, when the movement of the support arm device 400 is controlled by force control, a torque sensor can be provided preferably in the actuator 300, in order to detect the force exerted on the arm unit 420.

(2-3. Configuration of Brake Mechanism)

With reference to FIGS. 4 and 5, the configuration of the brake mechanism 370 according to the present embodiment will be described in detail. FIG. 4 is a perspective cross-sectional view illustrating the configuration of the brake mechanism 370 according to the present embodiment. FIG. 5 is an explanatory diagram for describing the movement of the brake mechanism 370 according to the present embodiment. Note that the brake mechanism 370 is what is called a dry multi-plate electromagnetic brake.

FIG. 4 illustrates a perspective cross-sectional view of the brake mechanism 370 that is cut off on a flat plane passing through its center axis. Referring to FIG. 4, the brake mechanism 370 includes a base member 371, an armature 374, and a hub 376, which have substantially disk shapes and are stacked in the rotation shaft direction (x axis direction). The base member 371, the armature 374, and the hub 376 are each provided with an opening at the substantially center of the disk shape, and the rotation shaft of the actuator 300 is inserted into the opening (the rotation shaft of the motor 310 in the example illustrated in FIG. 3).

The hub 376 is engaged fixedly with the rotation shaft of the actuator 300, and rotates with the rotation shaft of the actuator 300 by the driving of the actuator 300. On the other hand, the base member 371 and the armature 374 are connected to the rotation shaft of the actuator 300 via a bearing (not illustrated in the drawings). Also, the armature 374 is configured movable in the rotation shaft direction between the base member 371 and the hub 376.

Further, a disk 375 and a plate 377 of substantially annular shape are provided on the outer circumference of the hub 376. In the region corresponding to the outer circumference of the hub 376, the armature 374, the disk 375, and the plate 377 are stacked in this order in the rotation shaft direction.

The hub 376 and the disk 375 are combined with a spline, and the hub 376 and the disk 375 integrally rotate with the rotation shaft of the actuator 300. On the other hand, the plate 377 is connected to the base member 371 and the armature 374 by a bolt 378, not through the hub 376. That is, in the brake mechanism 370, only the hub 376 and the disk 375, among the depicted components, rotate with the rotation shaft of the actuator 300.

A coil 372 is provided in the inner portion of the base member 371. Also, the base member 371 and the armature 374 are connected by a spring (not illustrated in the drawings). The armature 374 moves in the rotation shaft direction by the magnetic force by the electrical current applied to the coil 372 and the restoring force of the spring, in order to achieve unlocking and locking of the brake.

With reference to FIG. 5, the movement of the brake mechanism 370 will be described. FIG. 5 illustrates a cross section passing through the center axis of configuration of the brake mechanism 370, particularly only a half of the configuration with respect to the center axis, for simplicity. Also, FIG. 5 schematically illustrates a spring 379, which is omitted in FIG. 4.

FIG. 5 (a) illustrates the state of the brake mechanism 370, when electricity is supplied, that is, when the electric power is supplied to the coil 372. This corresponds to a state in which the locking of the rotation shaft of the actuator 300 by the brake mechanism 370 is released.

As illustrated in FIG. 5 (a), when electricity is supplied, the armature 374 moves in the rotation shaft direction so as to be pulled toward the base member 371 by the magnetic force generated by supplying electricity to the coil 372. Thereby, the armature 374, the disk 375, and the plate 377 have a predetermined gap from each other in the rotation shaft direction. When the rotation shaft of the actuator 300 rotates, the hub 376 and the disk 375 rotate together, but the armature 374, the disk 375, and the plate 377 do not contact each other, and thus the disk 375 rotates idly, and the brake force is not exerted on the rotation of the actuator 300. Note that, in this case, the spring 379 connecting the base member 371 and the armature 374 is in a compressed state by the armature 374 that is pulled toward the base member 371.

FIG. 5 (b) illustrates the state of the brake mechanism 370 when electricity is not supplied, that is when the electric power is not supplied to the coil 372. This corresponds to the state in which the rotation shaft of the actuator 300 is locked by the brake mechanism 370.

When electricity is not supplied, the magnetic force generated by supplying electricity to the coil 372 disappears, and thus the armature 374 moves in the rotation shaft direction so as to get away from the base member 371 by the restoring force of the spring 379, as illustrated in FIG. 5 (b). Thereby, the disk 375 is pressed on the plate 377 by the armature 374. Thus, the rotation of the disk 375 is stopped, that is, the rotation of the rotation shaft of the actuator 300 is stopped, by the static frictional force generated between the disk 375 and the plate 377.

Here, as described above, in the present embodiment, the brake force of the brake mechanism 370 is adjusted to support the weight of the arm unit 420 to keep the orientation of the arm unit 420 when electricity is not supplied, and to rotate the rotation shaft in response to the external force when the external force equal to or larger than a predetermined value is loaded. As described above, the brake force in the brake mechanism 370 is a static frictional force generated between the disk 375 and the plate 377, and thus in the present embodiment the brake force of the brake mechanism 370 can be adjusted to satisfy the above condition by adjusting the matters that define the magnitude of the static frictional force.

For example, the brake force of the brake mechanism 370 can be adjusted by adjusting at least one of the contact area between the disk 375 and the plate 377, the static friction coefficient of the contacting surface between the disk 375 and the plate 377, and the restoring force of the spring 379.

Note that, specifically, the brake force of the brake mechanism 370 can be decided to keep the orientation of the arm unit 420, even in the worst orientation in which the maximum stress according to the weight of the arm unit 420 can be exerted on the actuator 300 (that is, the joint portions 421a to 421f). The force exerted on the actuator 300 in the worst orientation can be calculated by performing the simulation using a calculation model that simulates the structure of the arm unit 420. The above each components of the brake mechanism 370 are designed specifically to generate the static frictional force (that is, the brake force) that can endure the calculated force.

Also, the brake force of the brake mechanism 370 may be changed, depending on the position at which the brake mechanism 370 is provided in the arm unit 420. For example, as the position gets closer to the distal end in the arm unit 420, the components to be support at the joint portions 421a to 421f get lighter, and therefore the brake force for keeping the orientation of the arm unit 420 becomes smaller in the brake mechanism 370 of the actuator 300 provided closer to the distal end, as compared with the brake mechanism 370 of the actuator 300 provided closer to the proximal side. Thus, the brake force of the brake mechanism 370 may be differentiated in such a manner that the brake mechanism 370 of the actuator 300 provided closer to the distal end has a smaller brake force. As described above, the brake force is designed precisely by adjusting the brake force for each brake mechanism 370, and thus the behavior of the arm unit 420 when electricity is not supplied (stop of the arm unit 420 and the movement of the arm unit 420 by manual operation) is achieved more appropriately. Note that, the optimal value of the brake force of each brake mechanism 370 according to the location position in the arm unit 420 may be calculated by performing repetitively the simulation in consideration of the above worst orientation with different brake forces.

In the above, with reference to FIGS. 4 and 5, the configuration of the brake mechanism 370 according to the present embodiment has been described. In the present embodiment, the above brake mechanism 370 is mounted on each joint portion 421a to 421f of the support arm device 400. As described above, the brake mechanism 370 is configured in such a manner to fix the joint portions 421a to 421f and keep the orientation of the arm unit 420, when the supply of the electric power is stopped. Thus, for example, even in the time of emergency such as power outage, the movement of the arm unit 420 is stopped safely. Also, in the brake mechanism 370, the brake force is adjusted to allow the movement of the joint portions 421a to 421f when the external force equal to or larger than a predetermined value is exerted, even if the supply of the electric power is disrupted, and the brake operates. Thus, even when the power supply is lost, the arm unit 420 can be moved manually to continue the surgical operation. As described above, according to the present embodiment, safety is improved more in the support arm device 400.

(3. Specific Example of Setting Method of Brake Force)

Here, a setting method of the brake force of the above brake mechanism 370 will be described in more detail. FIG. 6 is a diagram for describing the setting method of the brake force of the brake mechanism 370.

As described above, the brake force of the brake mechanism 370 can be decided to keep the orientation of the arm unit even in the worst orientation. FIG. 6 schematically illustrates the configuration from the distal end of the arm unit 20 to the second shaft in the worst orientation. In the exemplary configuration illustrated in FIG. 6, the arm unit 20 includes, at the vicinity of the distal end, an image capturing unit 201 provided at the distal end, a joint portion 203 that supports the image capturing unit 201 in a rotatable manner with respect to the rotation shaft (axis $O_1$) in substantially parallel with the optical axis, a link 205 that extends in the direction in substantially parallel with the axis $O_1$ and supports the joint portion 203 at the distal end, a joint portion 207 that supports the link 205 in a rotatable manner with respect to the rotation shaft (axis $O_2$) substantially perpendicular to the extension direction, and a link 209 that extends in the direction substantially perpendicular to the axis $O_2$ and supports the joint portion 207 at the distal end. In FIG. 6, the joint portions 203, 207 are depicted simply these joint portions 203, 207 include the actuator 300, that is, the brake mechanism 370 illustrated in FIG. 3, in the same way as the joint portions 421a to 421f illustrated in FIG. 2. Also, the image capturing unit 201 is a video microscope, in the same way as the image capturing unit 423 illustrated in FIG. 2.

Here, as one example, in the configuration illustrated in FIG. 6, a case when setting the brake force of the brake mechanism 370 provided in the joint portion 207 corresponding to the axis $O_2$ which is the rotation shaft of the second shaft will be described. Specifically, as illustrated in FIG. 6, the worst orientation of the arm unit 20 with respect to the joint portion 207 is a horizontal orientation of the configuration closer to the distal end than the joint portion 207 supported by the joint portion 207 (the configuration surrounded by dashed line in the drawing. in the following, referred to as distal end component 211). In this orientation, the largest stress for supporting the own weight of the distal end component 211 is exerted on the joint portion 207.

The brake force of the brake mechanism 370 of the joint portion 207 is decided to keep the orientation of the arm unit 20, that is, to support the distal end component 211, when electricity is not supplied, even in this worst orientation. Specifically, where the gravity force exerted on the distal end component 211 is α (N), and the distance between the gravity center 213 of the distal end component 211 in the worst orientation and the rotation shaft axis $O_2$ of the joint portion 207 is L (m), the brake force to support a moment of magnitude α×L is to be exerted on the brake mechanism 370 of the joint portion 207, in order to keep the orientation of the arm unit 20 when electricity is not supplied. Thus, the brake force of the brake mechanism 370 of the joint portion 207 is decided to support at least a value generated by adding a margin to the magnitude of the moment. As described above, the brake force of the brake mechanism 370 can be decided according to the weight of the components provided closer to the distal end than the joint portion 207 in which the brake mechanism 370 is provided (that is, the distal end component 211) and the distance between the gravity center 213 of the distal end component 211 and the rotation shaft axis $O_2$ of the joint portion 207.

For example, as a result of design of an exemplary preferable configuration of the present embodiment which was made actually by the present inventors, the gravity force α exerted on the distal end component 211 is approximately 5.0 (N), when the weight of the image capturing unit 201 is approximately 300 (g) to 500 (g), and the distance L between the gravity center 213 of the distal end component 211 and the rotation shaft axis $O_2$ of the joint portion 207 is approximately 0.1 (m). In this case, the brake mechanism 370 of the joint portion 207 is to have at least the brake force that can support the moment of α×L=5.0 (N)×0.1 (m)=0.5 (N·m). Thus, for example, assuming that the margin is 0.5 (N·m), the brake force of the brake mechanism 370 of the joint portion 207 may be set at a value that can support the moment of 0.5 (N·m)+0.5 (N·m)=1.0 (N·m).

(4. Exemplary Variant of Brake Mechanism)

In the embodiment described above, the brake mechanism 370 utilizes the magnetic force generated by supplying electricity to the coil 372 and the restoring force of the spring 379. However, in the present embodiment, the specific configuration of the brake mechanism 370 is not limited to such an example. In the present embodiment, any type of brake mechanism may be used if the brake mechanism has a function for locking the rotation shaft of the actuator 300 when electricity is not supplied and releasing the locking when electricity is supplied, and the brake mechanism can adjust the brake force. Here, other exemplary configurations of the brake mechanism 370 will be described as several exemplary variants of the present embodiment.

Note that, with respect to the brake mechanism according to each exemplary variant described below, the same matters as the matters described with respect to the brake mechanism 370 in the above embodiment can be applied as far as possible. For example, in the same way as the above embodiment, the brake force of the brake mechanism according to each exemplary variant may be changed depending on the position at which the brake mechanism is provided in the arm unit 420. Also, the brake mechanism according to the present exemplary variant in which the brake force is adjusted is needless to be provided in all joint portions 421*a* to 421*f*, but the brake force may be adjusted only in the brake mechanisms provided in the joint portions that enable the movement for continuing the surgical operation (for example, the joint portions 421*d* to 421*f* provided in the distal side).

(4-1. Brake Using Oil Hydraulic Cylinder)

With reference to FIG. 7, the configuration of the brake mechanism according to one exemplary variant of the present embodiment will be described. FIG. 7 is a cross-sectional view illustrating the configuration of the brake mechanism according to one exemplary variant of the present embodiment. FIG. 7 illustrates a cross-sectional view of the brake mechanism according to the present exemplary variant that is cut off on the flat plane passing through the center axis. The brake mechanism illustrated in FIG. 7 is mounted on the actuator 300 instead of the brake mechanism 370 described with reference to FIG. 4, and can be mounted on each joint portion 421*a* to 421*f* of the support arm device 400 according to the present embodiment.

Referring to FIG. 7, the brake mechanism according to the present exemplary variant 380 is configured such that a housing 383 is combined via a bearing 382 on the outer circumference of a rotation shaft 381. The rotation shaft 381 corresponds to the rotation shaft of the motor 310 of the actuator 300.

In the housing 383, a plurality of plates 384 of disk shape and a plurality of disks 385 of same disk shape are provided. The plates 384 and the disks 385 are provided with the openings at the substantially center of the disk shape, and the rotation shaft 381 is inserted into the openings. As illustrated in the drawing, the plates 384 and the disks 385 are stacked alternatingly in the direction of the rotation shaft 381. Although in FIG. 7 all of the stacked plates 384 and disks 385 are in contact with each other for simplicity, predetermined gaps are actually provided between the plates 384 and the disks 385 to allow the movement described below when electricity is supplied and when electricity is not supplied.

The disks 385 are combined to the rotation shaft 381 with a spline, and rotate with the rotation shaft 381. On the other hand, the plates 384 is connected fixedly to a cylinder 386 provided in the housing 383. The cylinder 386 is configured movable in the rotation shaft 381 direction in the housing 383, by the oil hydraulic pressure exerted via an opening 389 provided in the housing 383.

A press plate 387 that presses the cylinder 386 in the rotation shaft 381 direction is provided at one end side of the cylinder 386 in the rotation shaft 381 direction. The press plate 387 is connected to the housing 383 by a spring 388, and the cylinder 386 is pressed by the press plate 387 by the restoring force of the spring 388, so that the cylinder 386 moves in the rotation shaft 381 direction. That is, the cylinder 386 and the plates 384 connected to the cylinder 386 are configured movable in the rotation shaft 381 direction, by the oil hydraulic pressure and the restoring force of the spring 388.

In the same way as the brake mechanism 370, the brake mechanism 380 has a function for locking the rotation shaft of the actuator 300 when electricity is not supplied and releasing the locking when electricity is supplied.

When electricity is supplied (that is, when the brake is unlocked), the cylinder 386 is pressurized by a compressor (not illustrated) or the like, and moves toward the press plate 387 in the rotation shaft 381 direction (moves in the positive direction of x axis in the example illustrated in the drawings), while pressing the press plate 387. The plates 384 also move in the positive direction of x axis together with the cylinder 386, and as a result the plates 384 and the disks 385 have predetermined gaps from each other. Thus, when the rotation shaft 381 rotates, the disks 385 rotates idly, and thus the brake force is not exerted on the rotation of the rotation shaft 381. Note that, in this case, the spring 388 that connects the housing 383 and the press plate 387 is compressed by the press plate 387 pressed by the cylinder 386.

On the other hand, when electricity is not supplied (that is, when the brake is operated), there is no pressurization, and thus the force of the cylinder 386 pressing the press plate 387 is reduced. When the pressing force becomes smaller than the restoring force of the spring 388, the cylinder 386 is pressed by the press plate 387 by the restoring force of the spring 388, and the cylinder 386 moves in the negative direction of x axis, and the plates 384 is pressed on the disks 385. Thus, the rotation of the disks 385 is stopped, that is, the rotation of the rotation shaft 381 is stopped, by the static frictional force that is generated between the plates 384 and the disks 385.

Note that, in the same way as the above embodiment, even in the present exemplary variant, the brake force of the brake mechanism 380 is adjusted to support the weight of the arm unit 420 to keep the orientation of the arm unit 420 when electricity is not supplied and to rotate the rotation shaft of the actuator 300 in response to the external force when the external force equal to or larger than a predetermined value is loaded. As described above, the brake force of the brake mechanism 380 is a static frictional force generated between the disks 385 and the plates 384, and thus in the present exemplary variant the brake force of the brake mechanism 380 can be adjusted to satisfy the above condition by adjusting the matters that define the magnitude of the static frictional force.

For example, the brake force of the brake mechanism 380 can be adjusted by adjusting at least one of the contact area between the disks 385 and the plates 384, the static friction coefficient of the contacting surface between the disks 385 and the plates 384, and the restoring force of the spring 388. A specific brake force may be decided by the simulation in consideration of the worst orientation of the arm unit 420, in the same way as the above embodiment.

In the above, as one exemplary variant of the present embodiment, the brake mechanism 380 in which the brake operation is performed by the oil hydraulic pressure and the restoring force of the spring 388 when electricity is supplied and when electricity is not supplied has been described.

(4-2. Brake Using Magnetic Fluid)

With reference to FIG. 8, the configuration of the brake mechanism according to another exemplary variant of the present embodiment will be described. FIG. 8 is a cross-sectional view illustrating the configuration of the brake mechanism according to another exemplary variant of the present embodiment. FIG. 8 illustrates a cross-sectional view of the brake mechanism according to the present exemplary variant that is cut off on the flat plane passing through the center axis. The brake mechanism illustrated in FIG. 8 is mounted on the actuator 300 instead of the brake mechanism 370 described with reference to FIG. 4, and can be mounted on each joint portion 421*a* to 421*f* of the support arm device 400 according to the present embodiment.

Referring to FIG. 8, the brake mechanism according to the present exemplary variant 390 includes a disk 392 of disk shape fixedly connected to a rotation shaft 391, and a yoke member 393 provided opposite to the disk 392 in the rotation shaft 391 direction. The rotation shaft 391 corresponds to the rotation shaft of the motor 310 of the actuator 300. Also, the yoke member 393 is fixedly connected to a member that is relatively fixed to the rotation shaft 391, such as the housing of the motor 310 for example.

A coil 394 is provided in the inner portion of the yoke member 393. Also, two annular permanent magnets 395*a*, 395*b* that are fixedly connected in a concentric circle shape are provided on the surface of the disk 392 which is opposite to the yoke member 393. Further, magnetic fluid 396*a*, 396*b* are filled between the contact surfaces of the yoke member 393 and the permanent magnets 395*a*, 395*b*. The magnetic fluid 396*a*, 396*b* is, for example, a colloidal fluid in which a ferromagnetic powder (for example, fine particles of approximately 10 (nm)) is dispersed stably in a solution (for example, an organic solvent), and is linked by magnetism to form a solid-like or fixed state.

In the same way as the brake mechanism 370, the brake mechanism 390 has a function for locking the rotation shaft of the actuator 300 when electricity is not supplied and releasing the locking when electricity is supplied.

When electricity is not supplied (that is, when the brake is operated), the electrical current is not applied to the coil 394, and the magnetic flux that goes out from the permanent magnet 395*a* passes through the magnetic fluid 396*a*, the yoke member 393, the magnetic fluid 396*b*, the permanent magnet 395*b*, and the disk 392 in this order, and again returns to the permanent magnet 395*a*, in order to form a magnetic circuit. That is, when electricity is not supplied, a stronger magnetic field is generated in the magnetic fluid 396*a*, 396*b* than when electricity is supplied as described later. The magnetic fluid 396*a*, 396*b* is solidified by the magnetic field, and thus the disk 392 and the yoke member 393 are connected by the solidified magnetic fluid 396*a*, 396*b*. Thus, the rotation of the disk 392, that is, the rotation of the rotation shaft 391 is locked, and the brake is operated.

On the other hand, when electricity is supplied (that is, when the brake is unlocked), electrical current is applied to the coil 394 to generate the magnetic field in such a manner to cancel the magnetic field of the permanent magnets 395*a*, 395*b*. Thereby, the magnetic field applied to the magnetic fluid 396*a*, 396*b* is reduced, and the solidification of the magnetic fluid 396*a*, 396*b* is relaxed. Thus, even though the frictional force by the fluidized magnetic fluid 396*a*, 396*b* exists, the disk 392 is released from the yoke member 393, and thus the disk 392 rotates idly when the rotation shaft 381 rotates, and the brake force is not exerted on the rotation of the rotation shaft 391.

Note that, in the same way as the above embodiment, even in the present exemplary variant, the brake force of the brake mechanism 390 is adjusted to support the weight of the arm unit 420 to keep the orientation of the arm unit 420 when electricity is not supplied and to rotate the rotation shaft of the actuator 300 in response to the external force when the external force equal to or larger than a predetermined value is loaded. As described above, the brake force of the brake mechanism 390 is an adhesive force between the disk 392 and the yoke member 393 by the solidified magnetic fluid 396*a*, 396*b* (to be exact, the adhesive force between the permanent magnets 395*a*, 395*b* and the yoke member 393, via the permanent magnets 395*a*, 395*b*), and therefore in the present exemplary variant, the brake force of the brake mechanism 390 can be adjusted to satisfy the above condition, by adjusting the matters that define the magnitude of the adhesive force.

For example, the brake force of the brake mechanism 390 can be adjusted by adjusting at least one of the material of the magnetic fluid 396*a*, 396*b*, the contact area between the solidified magnetic fluid 396*a*, 396*b* and the yoke member 393, the contact area between the solidified magnetic fluid 396*a*, 396*b* and the disk 392 (to be exact, the permanent magnets 395*a*, 395*b*), and the magnetic force of the permanent magnets 395*a*, 395*b*. In the same way as the above embodiment, a specific brake force may be decided by the simulation in consideration of the worst orientation of the arm unit 420.

In the above, as another exemplary variant of the present embodiment, the brake mechanism 390 in which the brake operation is performed by the solidification of the magnetic fluid 396*a*, 396*b* when electricity is supplied and when electricity is not supplied has been described.

(5. Supplement)

The preferred embodiment of the present disclosure has been described above in detail with reference to the accompanying drawings, whilst the technical scope of the present disclosure is not limited to such an example. A person having ordinary knowledge in the technical field of the present disclosure obviously can conceive of various alterations and modifications within the scope of the technical concept recited in the appended claims, and it should be understood that they will naturally come under the technical scope of the present disclosure.

Also, the effects described in the present specification are only descriptive or illustrative, and are not restrictive. That is, the technology according to an embodiment of the present disclosure can have other effects that are obvious for a skilled person from the description of the present specification, in addition to or instead of the above effects.

For example, in the above embodiment, the observation unit is a video microscope, but the technology according to an embodiment of the present disclosure is not limited to such an example. For example, the observation unit may be an endoscope. Although the endoscope is inserted into a body cavity of a patient via a trocar, a gap exists between the endoscope lens tube and the trocar, and thus, if the orientation of the arm unit is not kept when losing the power supply, it is possible that the endoscope moves slightly, and the patient is subject to danger. In the brake mechanisms 370, 380, 390 according to the present embodiment, the orientation of the arm unit is kept when the power supply is lost, so as to prevent this danger. As described above, the configurations and the functions of the brake mechanisms 370, 380, 390 according to the present embodiment exercise their effect, when the observation unit is the endoscope.

Also, for example, as describe in the above embodiment, the support arm device 400 according to the present embodiment can be applied preferably to medical care use. However, the application range of the support arm device 400 according to the present embodiment is not limited to medical care, but may be other fields. For example, the technology according to the brake mechanisms 370, 380, 390 describe above may be applied to an industrial support arm device used in a plant or the like. By applying the technology to industrial use, the movement can be stopped safely, and the basic movements can be performed manually, at the time of emergency such as power outage, and thus the support arm device 400 of higher convenience can be configured. Also, the technology according to the brake mechanisms 370, 380, 390 described above may be applied more widely to any device including a plurality of joint portions that can be driven.

Additionally, the present technology may also be configured as below.

(1)

A medical support arm device including:

a brake mechanism provided in at least one of a plurality of joint portions configuring an arm unit, and configured to release a rotation shaft of the one of joint portions when electricity is supplied and lock the rotation shaft when electricity is not supplied, wherein the brake mechanism supports a weight of the arm unit to keep an orientation of the arm unit when electricity is not supplied, and has a brake force that allows rotation of the rotation shaft by an external force equal to or larger than a predetermined value.

(2)

The medical support arm device according to (1), wherein the brake force is decided to keep the orientation of the arm unit even in a worst orientation in which a maximum stress according to the weight of the arm unit is exerted on the joint portions.

(3)

The medical support arm device according to (1) or (2), wherein the brake force is adjusted to a value that varies depending on a position at which the brake mechanism is provided in the arm unit.

(4)

The medical support arm device according to any one of (1) to (3), wherein the brake force is adjusted to a smaller value, as the brake mechanism is located closer to a distal end of the arm unit.

(5)

The medical support arm device according to any one of (1) to (4), wherein the brake mechanism that supports the weight of the arm unit to keep the orientation of the arm unit when electricity is not supplied and has the brake force that allows rotation of the rotation shaft by the external force equal to or larger than the predetermined value is provided only in a joint portion that defines an orientation of a distal end unit provided at a distal end of the arm unit, among the plurality of joint portions.

(6)

The medical support arm device according to any one of (1) to (5), wherein the brake mechanism includes:

an armature configured to be movable in a direction of the rotation shaft by a magnetic force generated by supplying electricity to a coil and a restoring force of a spring;

a disk configured to rotate with the rotation shaft; and a plate provided opposite to the armature with the disk in between, wherein the rotation shaft is unlocked by moving the armature in such a manner that the armature, the disk, and the plate have predetermined gaps from each other, by the magnetic force generated by supplying electricity to the coil, when electricity is supplied, and wherein the rotation shaft is locked by moving the armature in such a manner to press the disk on the plate, by the restoring force of the spring, when electricity is not supplied.

(7)

The medical support arm device according to (6), wherein the brake force of the brake mechanism is adjusted by adjusting at least one of a contact area between the disk and the plate, a static friction coefficient of contacting surfaces of the disk and the plate, and the restoring force of the spring.

(8)

The medical support arm device according to any one of (1) to (5), wherein the brake mechanism includes:

a disk configured to rotate with the rotation shaft; and a cylinder connected to a plate provided opposite to the disk, and configured to be movable in a direction of the rotation shaft by an oil hydraulic pressure and a restoring force of a spring, wherein the rotation shaft is unlocked by moving the cylinder in such a manner that the disk and the plate have a predetermined gap from each other, by the oil hydraulic pressure, when electricity is supplied, and wherein the rotation shaft is locked by moving the cylinder in such a manner to press the plate on the disk, by the restoring force of the spring, when electricity is not supplied.

(9)

The medical support arm device according to (8), wherein the brake force of the brake mechanism is adjusted by adjusting at least one of a contact area between the disk and the plate, a static friction coefficient of contacting surfaces of the disk and the plate, and the restoring force of the spring.

(10)

The medical support arm device according to any one of (1) to (5), wherein the brake mechanism includes:

a disk configured to rotate with the rotation shaft;

a yoke member provided opposite to the disk in a direction of the rotation shaft and including a coil in an inner portion;

a permanent magnet provided on a surface of the disk which is opposite to the yoke member; and a magnetic fluid provided between the yoke member and the permanent magnet, and configured to solidify according to an intensity of an applied magnetic field, wherein solidification of the magnetic fluid is relaxed, and the rotation shaft is unlocked, by generating a magnetic field from the coil in such a manner to cancel a magnetic field of the permanent magnet, by supplying electricity to the coil, when electricity is supplied, and wherein the yoke member and the disk are connected by the solidified magnetic fluid, and the rotation shaft is locked, by solidifying the magnetic fluid by the magnetic field from the permanent magnet, when electricity is not supplied.

(11)

The medical support arm device according to (10), wherein the brake force of the brake mechanism is adjusted by adjusting at least one of a material of the magnetic fluid, a contact area between the solidified magnetic fluid and the yoke member, a contact area between the solidified magnetic fluid and the permanent magnet, and a magnetic force of the permanent magnet.

(12)

A medical observation device including:

an arm unit including a plurality of joint portions; and an observation unit provided at a distal end of the arm unit to observe a surgical site of a patient, wherein at least one of the plurality of joint portions is provided with a brake mechanism configured to release a rotation shaft of the one of joint portions when electricity is supplied and to lock the rotation shaft when electricity is not supplied, and wherein the brake mechanism supports a weight of the arm unit to keep an orientation of the arm unit when electricity is not supplied, and has a brake force that allows rotation of the rotation shaft by an external force equal to or larger than a predetermined value.

(13)

The medical observation device according to (12), further including:

a power supply control unit configured to control driving electric power supply to the arm unit and the observation unit, wherein the power supply control unit cuts off electric power supply to the arm unit, and supplies electric power preferentially to the observation unit, when an abnormality or a failure occurs in an electric power system.

(14)

A medical support arm device including:

a brake provided in at least one joint of a plurality of joints that define a deployment configuration of a multi-joint arm, and configured to release a rotation shaft of the at least one joint when electricity is supplied to the multi-joint arm and lock the rotation shaft when electricity is not supplied to the multi-joint arm, wherein when electricity is not supplied to the multi-joint arm, the brake is configured to exert a brake force that supports a weight of the multi-joint arm to maintain the deployment configuration of the multi-joint arm, but also permits rotation of the rotation shaft by an external manually applied force equal to or larger than a predetermined value.

(15)

The medical support arm device according to (14), wherein the brake force is equal to or greater than a supporting force to maintain the deployment configuration of the multi-joint arm even when a maximum stress caused by a weight of the multi-joint arm is exerted on at least one of the plurality of joints.

(16)

The medical support arm device according to (14), wherein the brake force has at least a supporting force to maintain the deployment configuration of the multi-joint arm even when the multi-joint arm is fully stretched out horizontally.

(17)

The medical support arm device according to (14), wherein the external manually applied force is a manual force by a hand of a user.

(18)

The medical support arm device according to (14), wherein the multi-joint arm is a power-assisted multi-joint arm.

(19)

The medical support arm device according to (15), wherein the brake force is controllably adjusted to correspond with a change in torque on the at least one of the joints depending on the deployment configuration of the multi-joint arm.

(20)

The medical support arm device according to (14), wherein a value of the brake force varies depending on a position at which the brake is provided in the multi-joint arm.

(21)

The medical support arm device according to (20), wherein the value of the brake force is smaller, as the brake is positioned closer to a distal end of the multi-joint arm.

(22)

The medical support arm device according to (14), wherein the brake is provided only in a joint that defines a deployment configuration of a distal end device provided at a distal end of the multi-joint arm.

(23)

The medical support arm device according to (14), wherein the brake includes:

an armature configured to be movable in a direction of the rotation shaft by a magnetic force generated by supplying electricity to a coil and returned by a restoring force of a spring;

a disk configured to rotate with the rotation shaft; and a plate disposed opposite to the armature with the disk disposed therebetween, wherein the rotation shaft is unlocked by a movement of the armature so as to create predetermined gaps between the armature, the disk, and the plate, the predetermined gaps being generated by the magnetic force, and the rotation shaft being locked by a movement of the armature so as to press the disk to the plate by the restoring force of the spring, when electricity is not supplied.

(24)

The medical support arm device according to (23), wherein the brake is controllably adjusted by setting at least one of a contact area between the disk and the plate, a static friction coefficient of contacting surfaces of the disk and the plate, and the restoring force of the spring.

(25)

The medical support arm device according to (14), wherein the brake includes:

a disk configured to rotate with the rotation shaft; and a cylinder connected to a plate disposed opposite to the disk, and configured to be moved in a direction of the rotation shaft by hydraulic pressure and returned by a restoring force of a spring, wherein the rotation shaft is unlocked by a movement of the cylinder so as to create a predetermined gap between the disk and the plate by the hydraulic pressure, when electricity is supplied, and the rotation shaft is locked by a movement of the cylinder so as to press the plate to the disk by the restoring force of the spring, when electricity is not supplied.

(26)

The medical support arm device according to (25), wherein the brake is controllably adjusted by setting at least one of a contact area between the disk and the plate, a static friction coefficient of contacting surfaces of the disk and the plate, and the restoring force of the spring.

(27)

The medical support arm device according to (14), wherein the brake includes:

a disk configured to rotate with the rotation shaft;

a yoke disposed opposite the disk in a direction of the rotation shaft and including a coil in an inner portion;

a permanent magnet disposed on a surface of the disk opposite the yoke member; and a magnetic fluid disposed between the yoke and the permanent magnet, and configured to solidify to a solidified magnetic material according to an intensity of an applied magnetic field, wherein at least partial solidification of the magnetic material is experienced, and the rotation shaft is unlocked, by generating a magnetic field from the coil so as to cancel a magnetic field of the permanent magnet, by supplying electricity to the coil, when electricity is supplied, and the yoke member and the disk are connected by the solidified magnetic material, and the rotation shaft is locked, by solidifying the magnetic fluid by the magnetic field from the permanent magnet, when electricity is not supplied.

(28)

The medical support arm device according to (27), wherein the brake is controllably adjusted by setting at least one of a material of the magnetic fluid, a contact area between the solidified magnetic material and the yoke, a contact area between the solidified magnetic material and the permanent magnet, and a magnetic force of the permanent magnet.

(29)

A medical system including:

a multi-joint arm including a plurality of joints; and a medical device provided at a distal end of the multi-joint arm to oppose a surgical site of a patient, wherein at least one of the plurality of joints is provided with a brake configured to release a rotation shaft of the at least one joint when electricity is supplied and to lock the rotation shaft when electricity is not supplied, and the brake is configured to support a weight of the multi-joint arm to maintain a deployment configuration of the multi-joint arm when electricity is not supplied, and apply a brake force that allows rotation of the rotation shaft by an external force equal to or larger than a predetermined value.

(30)

The medical system according to (29), wherein the medical device including observation optics aligned to provide an optical path through the observation optics, to the surgical site.

(31)

The medical system according to (30), wherein the medical device is an observation device that includes imaging circuitry disposed in at least one of a digital still camera or a video camera.

(32)

The medical system according to (31), further including:

power supply control circuitry configured to control a driving of an electric power supply to the multi-joint arm and the imaging circuitry, wherein the power supply control circuitry is configured to remove a supply of electricity from the electric power supply to the multi-joint arm, and preferentially supply electric power to the imaging circuitry, when an interruption of electrical power is experienced.

(33)

The medical system according to (32), wherein:

the brake force is equal to or greater than a supporting force to maintain the deployment configuration of the multi-joint arm even when a maximum stress caused by a weight of the multi-joint arm is exerted on at least one of the joints.

(34)

A medical support arm device further including:

a brake provided in at least one joint of a plurality of joints that define a deployment configuration of a multi-joint arm, and configured to release a rotation shaft of the at least one joint when electricity is supplied to the multi-joint arm and lock the rotation shaft when electricity is not supplied to the multi-joint arm, wherein when electricity is not supplied to the multi-joint arm, the brake is configured to exert a brake force that supports a weight of the multi-joint arm to maintain the deployment configuration of the multi-joint arm, but also permits rotation of the rotation shaft by an external manually applied force equal to or larger than a predetermined value.

(35)

The medical support arm device according to (34), wherein:

the brake force is equal to or greater than a supporting force to maintain the deployment configuration of the multi-joint arm even when a maximum stress caused by a weight of the multi-joint arm is exerted on at least one of the plurality of joints.

(36)

The medical support arm device according to (34), wherein:

the brake force has at least a supporting force to maintain the deployment configuration of the multi-joint arm even when the multi-joint arm is fully stretched out horizontally.

(37)

The medical support arm device according to (34), wherein:

the external manually applied force is a manual force by a hand of a user.

(38)

The medical support arm device according to (34), wherein:

the multi-joint arm is a power-assisted multi-joint arm.

(39)

The medical support arm device according to (35), wherein:

the brake force is controllably adjusted to correspond with a change in torque on the at least one of the joints depending on the deployment configuration of the multi-joint arm.

(40)

The medical support arm device according to (34), wherein:

a value of the brake force varies depending on a position at which the brake is provided in the multi-joint arm.

(41)

The medical support arm device according to (40), wherein:

the value of the brake force is smaller, as the brake is positioned closer to a distal end of the multi-joint arm.

(42)

The medical support arm device according to (41), wherein:

the brake is provided only in a joint that defines a deployment configuration of a distal end device provided at a distal end of the multi-joint arm.

(43)

The medical support arm device according to (42), wherein the brake includes:

an armature configured to be movable in a direction of the rotation shaft by a magnetic force generated by supplying electricity to a coil and returned by a restoring force of a spring;

a disk configured to rotate with the rotation shaft; and a plate disposed opposite to the armature with the disk disposed therebetween, wherein the rotation shaft is unlocked by a movement of the armature so as to create predetermined gaps between the armature, the disk, and the plate, the predetermined gaps being generated by the magnetic force, and the rotation shaft being locked by a movement of the armature so as to press the disk to the plate by the restoring force of the spring, when electricity is not supplied.

(44)

The medical support arm device according to (43), wherein:

the brake is controllably adjusted by setting at least one of a contact area between the disk and the plate, a static friction coefficient of contacting surfaces of the disk and the plate, and the restoring force of the spring.

(45)

The medical support arm device according to (34), wherein the brake includes:

a disk configured to rotate with the rotation shaft; and a cylinder connected to a plate disposed opposite to the disk, and configured to be moved in a direction of the rotation shaft by hydraulic pressure and returned by a restoring force of a spring, wherein the rotation shaft is unlocked by a movement of the cylinder so as to create a predetermined gap between the disk and the plate by the hydraulic pressure, when electricity is supplied, and the rotation shaft is locked by a movement of the cylinder so as to press the plate to the disk by the restoring force of the spring, when electricity is not supplied.

(46)

The medical support arm device according to (45), wherein:

the brake is controllably adjusted by setting at least one of a contact area between the disk and the plate, a static friction coefficient of contacting surfaces of the disk and the plate, and the restoring force of the spring.

(47)

The medical support arm device according to (34), wherein the brake includes:

a disk configured to rotate with the rotation shaft;

a yoke disposed opposite the disk in a direction of the rotation shaft and including a coil in an inner portion;

a permanent magnet disposed on a surface of the disk opposite the yoke member; and a magnetic fluid disposed between the yoke and the permanent magnet, and configured to solidify to a solidified magnetic material according to an intensity of an applied magnetic field, wherein at least partial solidification of the magnetic material is experienced, and the rotation shaft is unlocked, by generating a magnetic field from the coil so as to cancel a magnetic field of the permanent magnet, by supplying electricity to the coil, when electricity is supplied, and the yoke member and the disk are connected by the solidified magnetic material, and the rotation shaft is locked, by solidifying the magnetic fluid by the magnetic field from the permanent magnet, when electricity is not supplied.

(48)

The medical support arm device according to (37), wherein:

the brake is controllably adjusted by setting at least one of a material of the magnetic fluid, a contact area between the solidified magnetic material and the yoke, a contact area between the solidified magnetic material and the permanent magnet, and a magnetic force of the permanent magnet.

(49)

A medical system including:

a multi-joint arm including a plurality of joints; and a medical device provided at a distal end of the multi-joint arm to oppose a surgical site of a patient, wherein at least one of the plurality of joints is provided with a brake configured to release a rotation shaft of the at least one joint when electricity is supplied and to lock the rotation shaft when electricity is not supplied, and the brake is configured to support a weight of the multi-joint arm to maintain a deployment configuration of the multi-joint arm when electricity is not supplied, and apply a brake force that allows rotation of the rotation shaft by an external force equal to or larger than a predetermined value.

(50)

The medical system according to (49), wherein:

the medical device including observation optics aligned to provide an optical path through the observation optics, to the surgical site.

(51)

The medical system according to claim (50), wherein:

the medical device is an observation device that includes imaging circuitry disposed in at least one of a digital still camera or a video camera.

(52)

The medical system according to claim (49), further including:

power supply control circuitry configured to control a driving of an electric power supply to the multi-joint arm and the imaging circuitry, wherein the power supply control circuitry is configured to remove a supply of electricity from the electric power supply to the multi-joint arm, and preferentially supply electric power to the imaging circuitry, when an interruption of electrical power is experienced.

(53)

The medical system according to claim (49), wherein:
the brake force is equal to or greater than a supporting force to maintain the deployment configuration of the multi-joint arm even when a maximum stress caused by a weight of the multi-joint arm is exerted on at least one of the joints.

REFERENCE SIGNS LIST 300 actuator
310 motor
320 speed reducer
330 input shaft encoder
340 output shaft encoder
350 output shaft
360 housing
370, 380, 390 brake mechanism
400, 510 support arm device (observation device)
410, 511 base portion
420, 512 arm unit
421a to 421f, 513a to 513c joint portion
423, 515 image capturing unit

The invention claimed is:

1. A medical system comprising:
a multi-joint arm including a plurality of joints;
a medical observation device including imaging circuitry and provided at a distal end of the multi joint arm to oppose a surgical site of a patient; and
power supply control circuitry configured to control a driving of an electric power supply to the multi joint arm and the imaging circuitry, the power supply control circuitry is configured to remove a supply of electricity from the electric power supply to the multi-joint arm, and preferentially supply electric power to the imaging circuitry, when an interruption of electrical power is experienced,
wherein at least one of the plurality of joints is provided with a brake configured to release a rotation shaft of the at least one joint when electricity is supplied and to lock the rotation shaft when electricity is not supplied, and
the brake is configured to support a weight of the multi joint arm to maintain a deployment configuration of the multi joint arm when electricity is not supplied, and apply a brake force that allows rotation of the rotation shaft by an external force equal to or larger than a predetermined value.

2. The medical system according to claim 1, wherein the medical observation device includes observation optics aligned to provide an optical path through the observation optics, to the surgical site.

3. The medical system according to claim 1, wherein:
the brake force is equal to or greater than a supporting force to maintain the deployment configuration of the multi joint arm even when a maximum stress caused by a weight of the multi joint arm is exerted on at least one of the joints.

4. The medical system according to claim 1, wherein the brake force is equal to or greater than a supporting force to maintain the deployment configuration of the multi joint arm even when a maximum stress caused by a weight of the multi joint arm is exerted on at least one of the plurality of joints.

5. The medical system according to claim 1, wherein the brake force has at least a supporting force to maintain the deployment configuration of the multi joint arm even when the multi joint arm is fully stretched out horizontally.

6. The medical system according to claim 1, wherein the external applied force is a manual force cause by a user.

7. The medical system according to claim 1, wherein the multi joint arm is a power-assisted multi joint arm.

8. The medical system according to claim 4, wherein the brake force is controllably adjusted to correspond with a change in torque on the at least one of the joints depending on the deployment configuration of the multi joint arm.

9. The medical system according to claim 1, wherein a value of the brake force varies depending on a position at which the brake is provided in the multi joint arm.

10. The medical system according to claim 9, wherein the value of the brake force is smaller, as the brake is positioned closer to a distal end of the multi-joint arm.

11. The medical system according to claim 1, wherein the brake is provided only in a joint that defines a deployment configuration of a distal end device provided at a distal end of the multi joint arm.

12. The medical system according to claim 1, wherein the brake includes:
an armature configured to be movable in a direction of the rotation shaft by a magnetic force generated by supplying electricity to a coil and returned by a restoring force of a spring;
a disk configured to rotate with the rotation shaft; and
a plate disposed opposite to the armature with the disk disposed therebetween, wherein
the rotation shaft is unlocked by a movement of the armature so as to create predetermined gaps between the armature, the disk, and the plate, the predetermined gaps being generated by the magnetic force, and
the rotation shaft being locked by a movement of the armature so as to press the disk to the plate by the restoring force of the spring, when electricity is not supplied.

13. The medical system according to claim 12, wherein the brake is controllably adjusted by setting at least one of a contact area between the disk and the plate, a static friction coefficient of contacting surfaces of the disk and the plate, and the restoring force of the spring.

14. The medical system according to claim 1, wherein the brake includes:
a disk configured to rotate with the rotation shaft; and
a cylinder connected to a plate disposed opposite to the disk, and configured to be moved in a direction of the rotation shaft by hydraulic pressure and returned by a restoring force of a spring, wherein
the rotation shaft is unlocked by a movement of the cylinder so as to create a predetermined gap between the disk and the plate by the hydraulic pressure, when electricity is supplied, and
the rotation shaft is locked by a movement of the cylinder so as to press the plate to the disk by the restoring force of the spring, when electricity is not supplied.

15. The medical system according to claim 14, wherein the brake is controllably adjusted by setting at least one of a contact area between the disk and the plate, a static friction coefficient of contacting surfaces of the disk and the plate, and the restoring force of the spring.

16. The medical system according to claim 1, wherein the brake includes:
a disk configured to rotate with the rotation shaft;
a yoke disposed opposite the disk in a direction of the rotation shaft and including a coil in an inner portion;

a permanent magnet disposed on a surface of the disk opposite the yoke member; and a magnetic fluid disposed between the yoke and the permanent magnet, and configured to solidify to a solidified magnetic material according to an intensity of an applied magnetic field, wherein at least partial solidification of the magnetic material is experienced, and the rotation shaft is unlocked, by generating a magnetic field from the coil so as to cancel a magnetic field of the permanent magnet, by supplying electricity to the coil, when electricity is supplied, and the yoke member and the disk are connected by the solidified magnetic material, and the rotation shaft is locked, by solidifying the magnetic fluid by the magnetic field from the permanent magnet, when electricity is not supplied.

17. The medical system according to claim 16, wherein the brake is controllably adjusted by setting at least one of a material of the magnetic fluid, a contact area between the solidified magnetic material and the yoke, a contact area between the solidified magnetic material and the permanent magnet, and a magnetic force of the permanent magnet.

18. A medical support arm device comprising:

a brake provided in at least one joint of a plurality of joints that define a deployment configuration of a multi joint arm, and configured to release a rotation shaft of the at least one joint when electricity is supplied to the multi joint arm and lock the rotation shaft when electricity is not supplied to the multi joint arm, wherein when electricity is not supplied to the multi joint arm, the brake is configured to exert a brake force that supports a weight of the multi-joint arm to maintain the deployment configuration of the multi-joint arm, but also permits rotation of the rotation shaft by an external manually applied force equal to or larger than a predetermined value, the medical support arm device is an observation device that includes imaging circuitry; and power supply control circuitry configured to control a driving of an electric power supply to the multi joint arm and the imaging circuitry, the power supply control circuitry is configured to remove a supply of electricity from the electric power supply to the multi-joint arm, and preferentially supply electric power to the imaging circuitry, when an interruption of electrical power is experienced.

19. The medical support arm device according to claim 18, wherein the brake force is equal to or greater than a supporting force to maintain the deployment configuration of the multi joint arm even when a maximum stress caused by a weight of the multi joint arm is exerted on at least one of the plurality of joints.

20. The medical support arm device according to claim 18, wherein the brake force has at least a supporting force to maintain the deployment configuration of the multi joint arm even when the multi joint arm is fully stretched out horizontally.

* * * * *